United States Patent
Uemori et al.

(10) Patent No.: US 10,975,415 B2
(45) Date of Patent: Apr. 13, 2021

(54) METHODS OF UTILIZING THERMOSTABLE MISMATCH ENDONUCLEASE

(71) Applicants: TAKARA BIO INC., Shiga (JP); KYUSHU UNIVERSITY, NATIONAL UNIVERSITY CORPORATION, Fukuoka (JP); EDUCATIONAL CORPORATION KANSAI BUNRI SOUGOUGAKUEN, Shiga (JP)

(72) Inventors: Takashi Uemori, Otsu (JP); Yoshizumi Ishino, Fukuoka (JP); Takehiro Sagara, Minamishimabara (JP); Sonoko Ishino, Fukuoka (JP); Takeshi Yamagami, Fukuoka (JP); Tsuyoshi Shirai, Nagahama (JP)

(73) Assignees: TAKARA BIO INC., Shiga (JP); KYUSHU UNIVERSITY, NATIONAL UNIVERSITY CORPORATION, Fukuoka (JP); EDUCATIONAL CORPORATION KANSAI BUNRI SOUGOUGAKUEN, Shiga (JP)

( * ) Notice: Subject to any disclaimer, the term of this patent is extended or adjusted under 35 U.S.C. 154(b) by 460 days.

(21) Appl. No.: 15/507,796

(22) PCT Filed: Sep. 9, 2015

(86) PCT No.: PCT/JP2015/075603
§ 371 (c)(1),
(2) Date: Mar. 1, 2017

(87) PCT Pub. No.: WO2016/039377
PCT Pub. Date: Mar. 17, 2016

(65) Prior Publication Data
US 2017/0253909 A1    Sep. 7, 2017

(30) Foreign Application Priority Data
Sep. 11, 2014 (JP) .............................. JP2014-184934

(51) Int. Cl.
*C12Q 1/68* (2018.01)
*C12N 9/22* (2006.01)
*C12N 15/09* (2006.01)

(52) U.S. Cl.
CPC ............. *C12Q 1/68* (2013.01); *C12N 9/22* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 3,395,021 A | 7/1968 | Glicksman et al. | |
| 4,889,818 A | 12/1989 | Gelfand et al. | |
| 5,602,011 A * | 2/1997 | Luhm ................. | C12N 9/1252 435/194 |
| 5,922,539 A | 7/1999 | Modrich et al. | |
| 6,391,557 B1 | 5/2002 | Yeung | |
| 6,428,955 B1 | 8/2002 | Koster | |
| 7,135,291 B2 | 11/2006 | Sagawa et al. | |
| 2001/0053519 A1 | 12/2001 | Fodor | |
| 2002/0128215 A1 | 9/2002 | Thomann | |
| 2003/0148283 A1 | 8/2003 | Barany et al. | |
| 2003/0165898 A1 | 9/2003 | Todd | |
| 2004/0137451 A1 | 7/2004 | Sagawa et al. | |
| 2004/0185455 A1 | 9/2004 | Shimada et al. | |
| 2005/0059000 A1 | 3/2005 | Sagawa et al. | |
| 2006/0110765 A1 | 5/2006 | Wang | |
| 2006/0248617 A1 | 11/2006 | Imanaka et al. | |
| 2010/0055742 A1 | 3/2010 | Nakashima et al. | |
| 2010/0291548 A1 | 11/2010 | Sharaf et al. | |
| 2013/0149695 A1 | 6/2013 | Lee et al. | |
| 2013/0296192 A1 | 11/2013 | Jacobson | |
| 2013/0338933 A1 | 12/2013 | Deciu et al. | |
| 2014/0309142 A1 | 10/2014 | Tian | |
| 2016/0017300 A1 | 1/2016 | Matsumura et al. | |

FOREIGN PATENT DOCUMENTS

| | | |
|---|---|---|
| JP | 2000-511774 | 9/2000 |
| JP | 2003-518951 | 6/2003 |
| JP | 2004-526423 | 9/2004 |
| JP | 2004-298200 | 10/2004 |
| JP | 2007-295838 | 11/2007 |
| JP | 2007-319096 | 12/2007 |
| JP | 2008-48725 | 3/2008 |
| JP | 2008-520245 | 6/2008 |
| WO | 96/32500 | 10/1996 |
| WO | 97/46701 | 12/1997 |
| WO | 99/42595 | 8/1999 |
| WO | 00/56929 | 9/2000 |
| WO | 01/49877 | 7/2001 |
| WO | 01/62974 | 8/2001 |

(Continued)

OTHER PUBLICATIONS

Elshawadfy et al. (Frontiers in Micro, 2014, 5(224):1-14) (Year: 2014).*

(Continued)

*Primary Examiner* — Stephanie K Mummert
(74) *Attorney, Agent, or Firm* — Wenderoth, Lind & Ponack, L.L.P.

(57) ABSTRACT

A polypeptide having a mismatch endonuclease activity of recognizing a mismatch and cleaving the mismatch; a mismatch-specific cleavage reaction using the polypeptide; a method for removing an error in a nucleic acid amplification reaction utilizing the polypeptide; a method for inhibiting the amplification of a nucleic acid comprising a specific nucleotide sequence during a nucleic acid amplification reaction; and a method for detecting a nucleic acid having a single-nucleotide polymorphism mutation utilizing the inhibition method.

1 Claim, 13 Drawing Sheets
Specification includes a Sequence Listing.

(56) References Cited

FOREIGN PATENT DOCUMENTS

| WO | 02/44335 | | 6/2002 | | |
| WO | 03/048395 | | 6/2003 | | |
| WO | 2004/022736 | | 3/2004 | | |
| WO | WO-2004022736 | A1 * | 3/2004 | ........... | C07K 14/195 |
| WO | 2011/102802 | | 8/2011 | | |
| WO | 2013/116771 | | 8/2013 | | |
| WO | 2013/175815 | | 11/2013 | | |
| WO | 2014/142261 | | 9/2014 | | |
| WO | 2016/039377 | | 3/2016 | | |

OTHER PUBLICATIONS

Youil et al. (PNAS, 1995, 92:87-91) (Year: 1995).*
Tori et al. (PLoS One, 2013, 8(3):e58497, p. 1-9) (Year: 2013).*
Extended European Search Report dated Sep. 17, 2018 in European Patent Application No. 16768715.1.
English translation of International Search Report dated Jun. 14, 2016 in International (PCT) Application No. PCT/JP2016/058852.
Office Action dated Sep. 6, 2017 in European Application No. 14762697.2.
Todd et al., "Allele-specific Enrichment: A Method for the Detection of Low Level N-*ras* Gene Mutations in Acute Myeloid Leukemia", Leukemia, 5(2):160-161 (1991).
Kahn et al., "Rapid and sensitive nonradioactive detection of mutant K-*ras* genes via 'enriched' PCR amplification", Oncogene, 6(6):1079-1083 (1991).
Lee et al., "Mutant Enrichment with 3'-Modified Oligonucleotides: A Practical PCR Method for Detecting Trace Mutant DNAs", The Journal of Molecular Diagnostics, 13(6):657-668 (2011).
English translation of International Preliminary Report on Patentability dated Oct. 5, 2017 in International Application No. PCT/JP2016/058852.
U.S. Appl. No. 15/558,348, filed Sep. 14, 2017.
Japanese Office Action dated Apr. 25, 2017 issued in Japanese Patent Application No. 2016-129036 (with Machine English Translation).
Accession No. FOLKL8, Uniprot[online], Feb. 6, 2013, retrieved on Apr. 12, 2017, URL, http://www.uniprot.org/uniprot/FOLKL8.txt?version=12, 2 pages.
Accession No. Q57678, Uniprot[online], Nov. 28, 2012, retrieved on Apr. 12, 2017, URL, http://www.uniprot.org/uniprot/Q57678.txt?version=62, 2 pages.
Pauline Vannier et al., "Complete Genome Sequence of the Hyperthermophilic, Piezophilic, Heterotrophic, and Carboxydotrophic Archaeon *Thermococcus barophilus* MP", Journal of Bacteriology, 2011, vol. 193, No. 6, pp. 1481-1482.
Carol J. Bult et al., "Complete Genome Sequence of the Methanogenic Archaeon, *Methanococcus jannaschii*", Science, 1996, vol. 273, pp. 1058-1073.
Office Action dated Dec. 30, 2016 in Chinese Application No. 201480026443.6, with English translation.
Dongmei et al., "Correction of the Error in Chemical DNA Synthesis", Chemistry of Life, vol. 32, No. 1, (2012), pp. 34-38, with English translation.
Sonoko Ishino et al., "Identification of a mismatch-specific endonuclease in hyperthermophilic Archaea", Nucleic Acids Research, vol. 44, No. 7, Mar. 21, 2016, pp. 2977-2986.
Extended European Search Report dated Oct. 27, 2016 in European Application No. 14762697.2.
Office Action dated Nov. 17, 2015 in Japanese Application No. 2015-505565, with English translation.
Kari et al., "Generation of targeted *Chlamydia trachomatis* null mutants", PNAS, vol. 108, No. 17, Apr. 26, 2011, pp. 7189-7193.

International Preliminary Report on Patentability dated Sep. 15, 2015 in International (PCT) Application No. PCT/JP2014/056738.
Smith et al., "Mutation detection with MutH, MutL, and MutS mismatch repair proteins", Proc. Natl. Acad. Sci. USA, vol. 93, Apr. 1996, pp. 4374-4379.
Bridger et al., Database Uniprot [online], Accession No. I6U8Z8, uploaded Oct. 3, 2012, 1 page.
Maeder et al., Database Uniprot [online], Accession No. Q8U4R1, uploaded Jun. 1, 2002, 2 pages.
International Search Report dated May 20, 2014 in International (PCT) Application No. PCT/JP2014/056738.
International Preliminary Report on Patentability dated Mar. 14, 2017 issued in International Patent Application No. PCT/JP2015/075603.
RecName: Full=Endonuclease NucS, Database NCBI Protein [online], May 14, 2014, Accession No. Q5JER9.
Pavel A. Zhulidov et al., "Simple cDNA normalization using kamchatka crab duplex-specific nuclease", Nucleic Acids Research, 2004, vol. 32, No. 3, e37, pp. 1-8.
Andrew Hillmann et al., "cDNA Amplification by SMART-PCR and Suppression Subtractive Hybridization (SSH)-PCR", Methods in Molecular Biology, DNA and RNA Profiling in Human Blood: Methods and Protocols, 2009, vol. 496, pp. 223-243.
Robyn Ward et al., "Restriction Endonuclease-Mediated Selective Polymerase Chain Reaction—A Novel Assay for the Detection of K-ras Mutations in Clinical Samples", American Journal of Pathology, 1998, vol. 153, No. 2, pp. 373-379.
Yumani Kuba et al., "Comparative analyses of the two proliferating cell nuclear antigens from the hyperthermophilic archaeon, Thermococcus kodakarensis", Genes to Cells, 2012, vol. 17, No. 11, pp. 923-937.
International Search Report dated Oct. 13, 2015 issued in International Patent Application No. PCT/JP2015/075603.
Extended European Search Report dated Feb. 12, 2018 issued in corresponding European Patent Application No. 15839690.3.
Nishioka et al., "Characterization of two intein homing endonucleases encoded in the DNA polymerase gene of *Pyrococcus kodakaraensis* strain KOD1", Nucleic Acids Research, 1998, vol. 26, No. 19, pp. 4409-4412.
Mean et al., "Modification of the enzyme mismatch cleavage method using T7 endonuclease I and silver staining", BioTechniques, 2004, vol. 36, No. 5, pp. 758-760.
Qiu, et al., "Mutation detection using Surveyor™ nuclease", BioTechniques, 2004, vol. 36, No. 4, pp. 702-707.
Office Action dated Jan. 12, 2018 issued in U.S. Appl. No. 14/773,915.
Sharon Begley, "Psst, the human genome was never completely sequenced. Some scientists say it should be", STATNews.com, Jun. 20, 2017, 8 pages.
Michael Anissimov, "How many species of bacteria are there?", WiseGeek.com, accessed Jan. 21, 2014, 2 pages.
"List of sequenced bacterial genomes", Wikpedia.com; accessed Jan. 24, 2014, 57 pages.
Office Action dated Sep. 10, 2019 in corresponding Japanese Patent Application No. 2017-508335, with English Machine Translation.
Office Action dated Nov. 5, 2019 in corresponding Chinese Patent Application No. 201580048826.8, with English Translation.
Xiang et al., "Role of PCNA in DNA repair", Chemistry of Life, 2009, vol. 29, No. 4, pp. 472-476, with English translation.
Office Action dated Sep. 1, 2020 in related U.S. Appl. No. 15/558,348, 24 pages.
Office Action dated Sep. 3, 2020, in corresponding Chinese Patent Application No. 201580048826.8, with English translation.
Ren et al., "Structure and function of a novel endonuclease acting on branched DNA substrates", The EMBO Journal, 2009, vol. 28, No. 16, pp. 2479-2489.
Office Action dated Apr. 14, 2020 in Japanese Patent Application No. 2017-508335, with English translation.

* cited by examiner

[Fig.1]
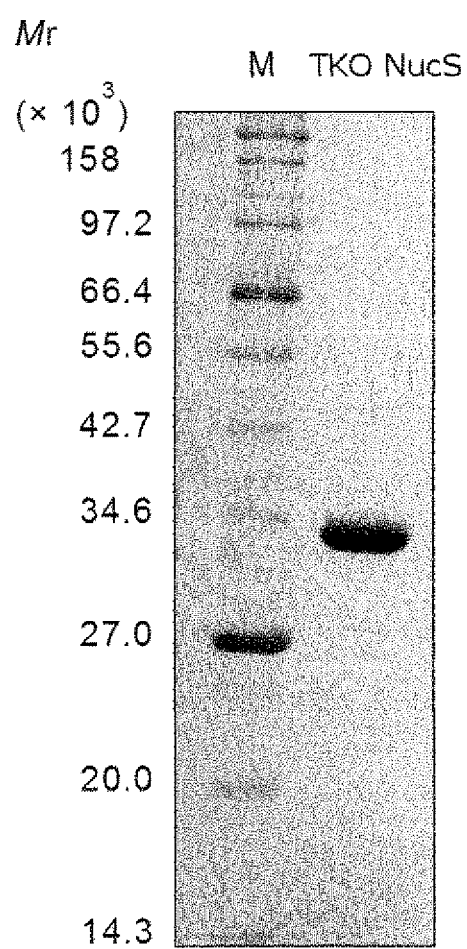

[Fig.2]

all match dsDNA (Cy5-45-nondamaged + temp45-normal)

Cy5 — 5'- CGAACTGCCTGGAATCCTGACGACATGTAGCGAACGATCACCTCA -3'
       3'- GCTTGACGGACCTTAGGACTGCTGTACATCGCTTGCTAGTGGAGT -5'

A-A dsDNA (Cy5-45-nondamaged + temp45-21A)

Cy5 — 5'- CGAACTGCCTGGAATCCTGACGACATGTAGCGAACGATCACCTCA -3'
       3'- GCTTGACGGACCTTAGGACTGCTGAACATCGCTTGCTAGTGGAGT -5'

A-C dsDNA (Cy5-45-nondamaged + temp45-21C)

Cy5 — 5'- CGAACTGCCTGGAATCCTGACGACATGTAGCGAACGATCACCTCA -3'
       3'- GCTTGACGGACCTTAGGACTGCTGCACATCGCTTGCTAGTGGAGT -5'

A-G dsDNA (Cy5-45-nondamaged + temp45-21G)

Cy5 — 5'- CGAACTGCCTGGAATCCTGACGACATGTAGCGAACGATCACCTCA -3'
       3'- GCTTGACGGACCTTAGGACTGCTGGACATCGCTTGCTAGTGGAGT -5'

G-T dsDNA (Cy5-45-mismatch + temp45-normal)

Cy5 — 5'- CGAACTGCCTGGAATCCTGACGACGTGTAGCGAACGATCACCTCA -3'
       3'- GCTTGACGGACCTTAGGACTGCTGTACATCGCTTGCTAGTGGAGT -5'

G-G dsDNA (Cy5-45-mismatch + temp45-21G)

Cy5 — 5'- CGAACTGCCTGGAATCCTGACGACGTGTAGCGAACGATCACCTCA -3'
       3'- GCTTGACGGACCTTAGGACTGCTGGACATCGCTTGCTAGTGGAGT -5'

T-C dsDNA (Cy5-45-temp45 + 45-mismatch25C)

Cy5 — 5'- TGAGGTGATCGTTCGCTACATGTCGTCAGGATTCCAGGCAGTTCG -3'
       3'- ACTCCACTAGCAAGCGATGTCCAGCAGTCCTAAGGTCCGTCAAGC -5'

T-T dsDNA (Cy5-45-temp45 + 45-mismatch25T)

Cy5 — 5'- TGAGGTGATCGTTCGCTACATGTCGTCAGGATTCCAGGCAGTTCG -3'
       3'- ACTCCACTAGCAAGCGATGTTCAGCAGTCCTAAGGTCCGTCAAGC -5'

C-C dsDNA (Cy5-45- temp45 + 45-mismatch22C)

Cy5 — 5'- TGAGGTGATCGTTCGCTACATGTCGTCAGGATTCCAGGCAGTTCG -3'
       3'- ACTCCACTAGCAAGCGATGTACCCAGTCCTAAGGTCCGTCAAGC -5'

[Fig.3]
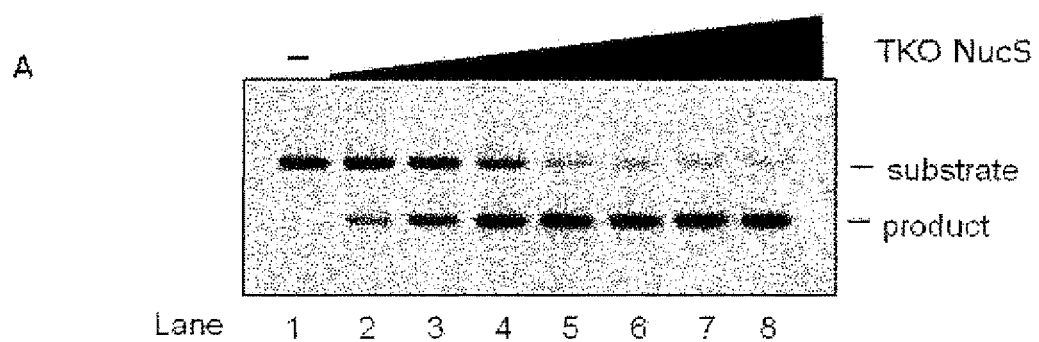
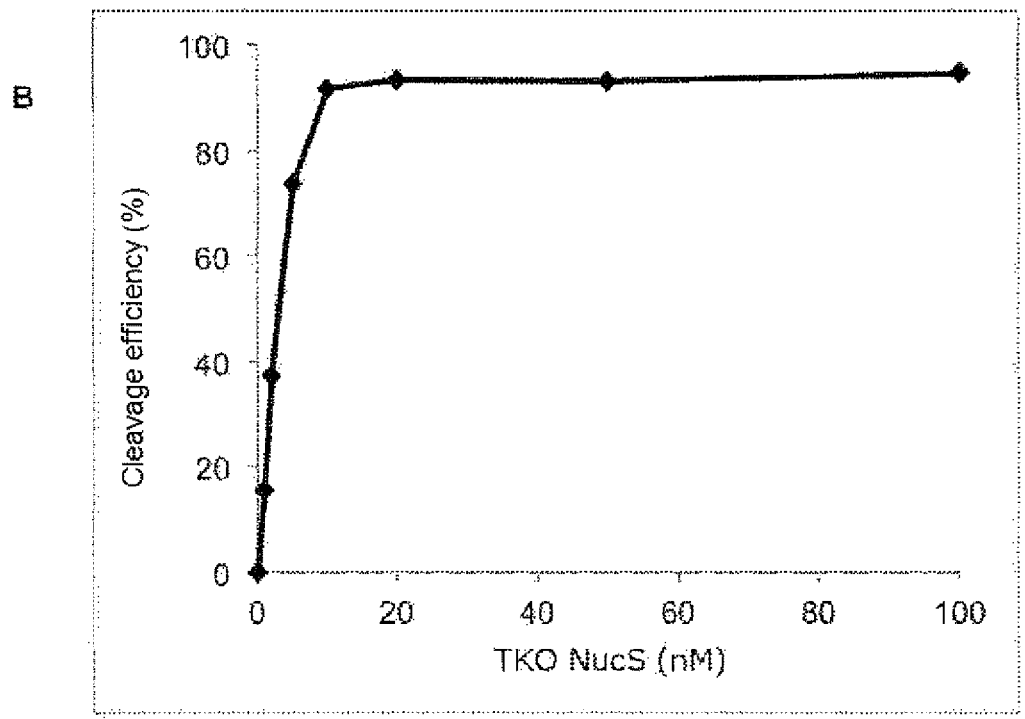

[Fig. 4]
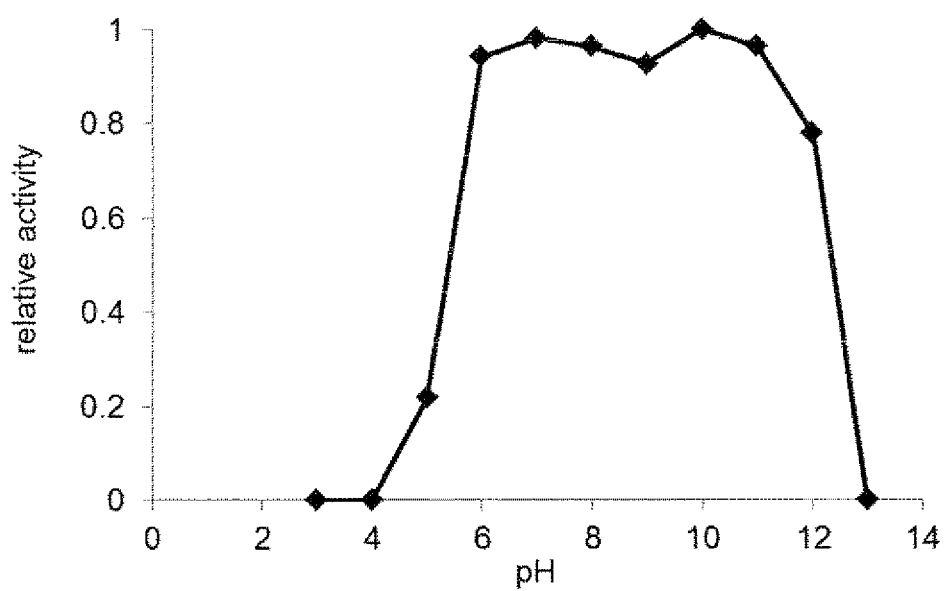

[Fig. 5]
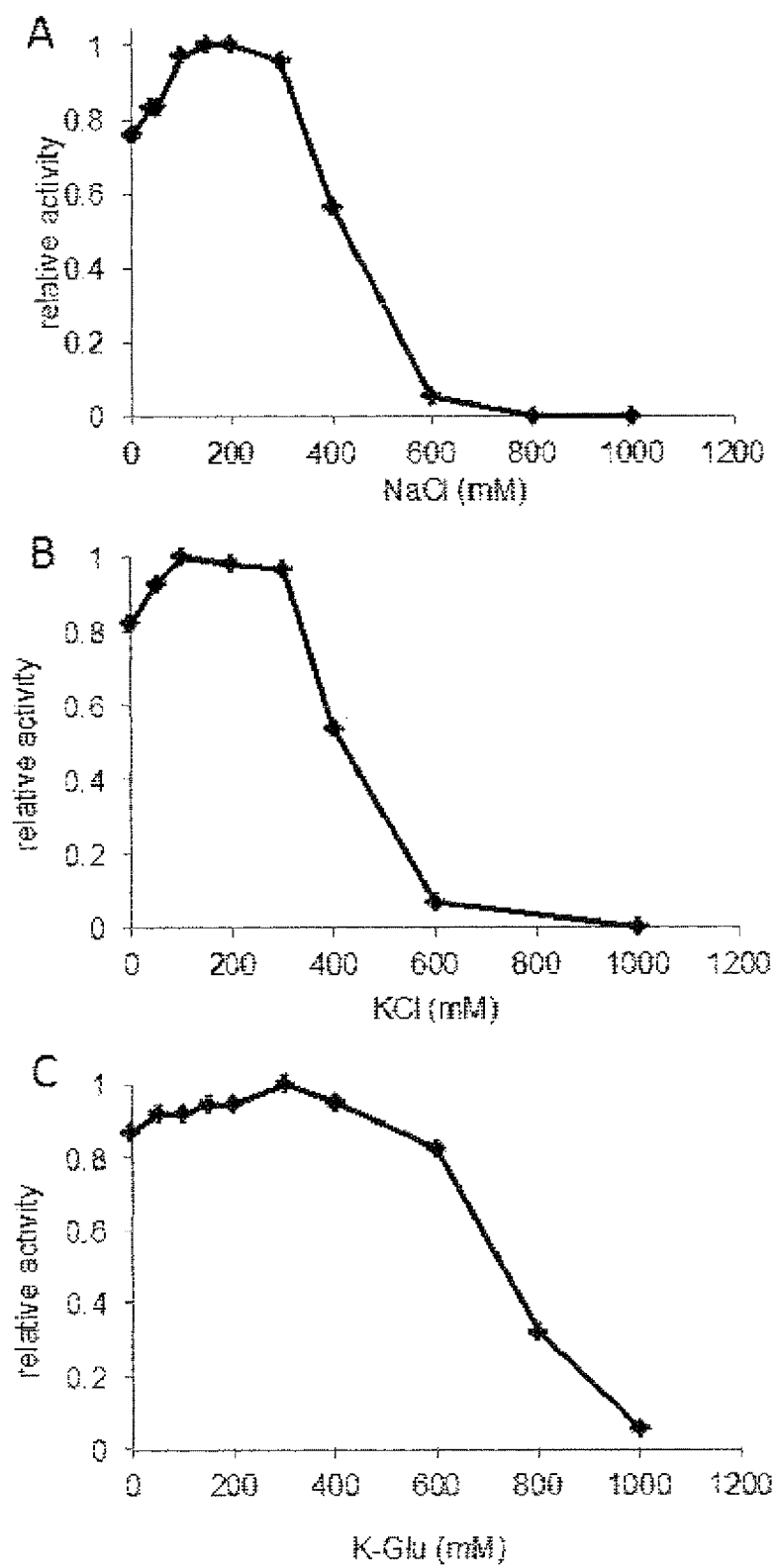

[Fig. 6]
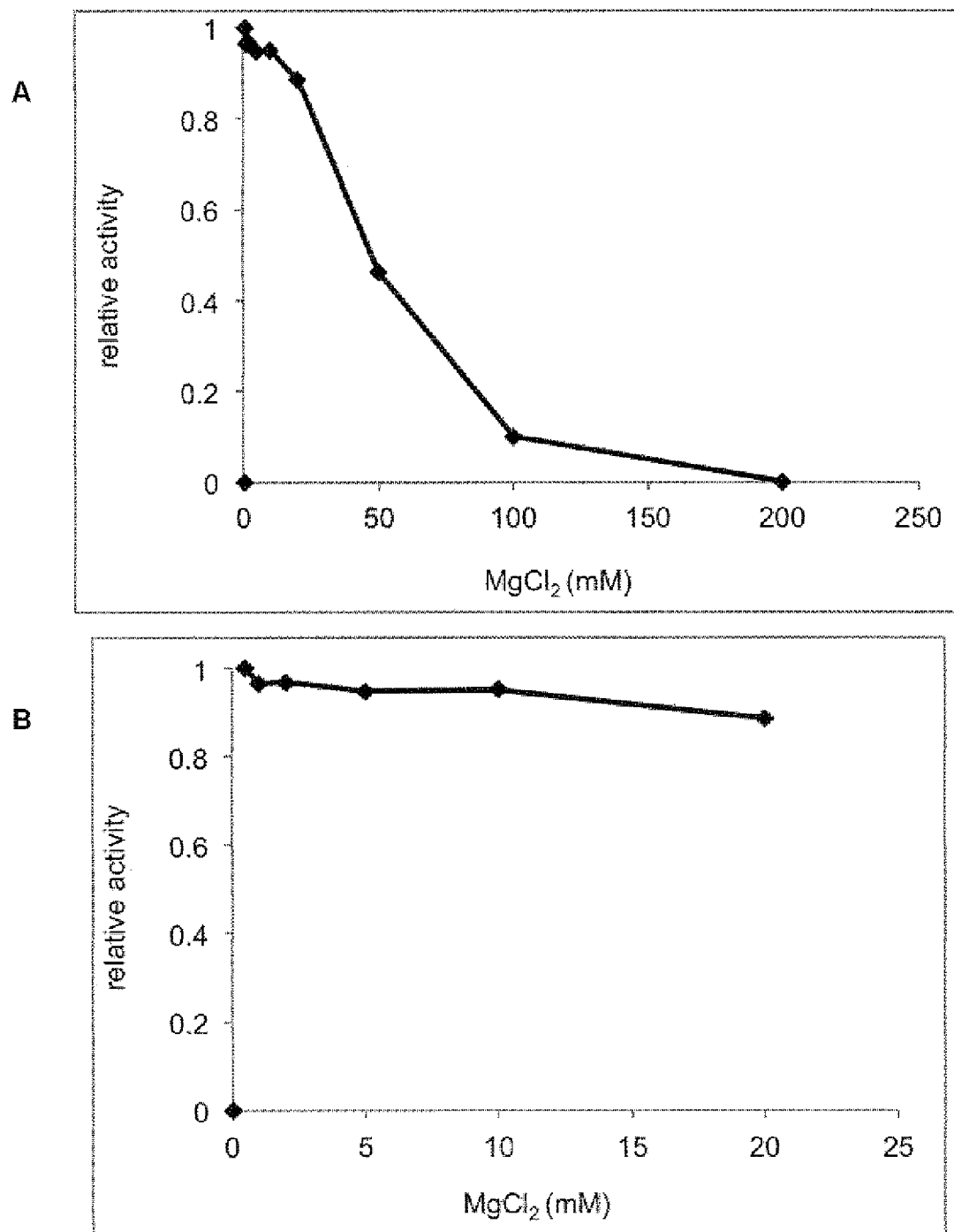

[Fig. 7]
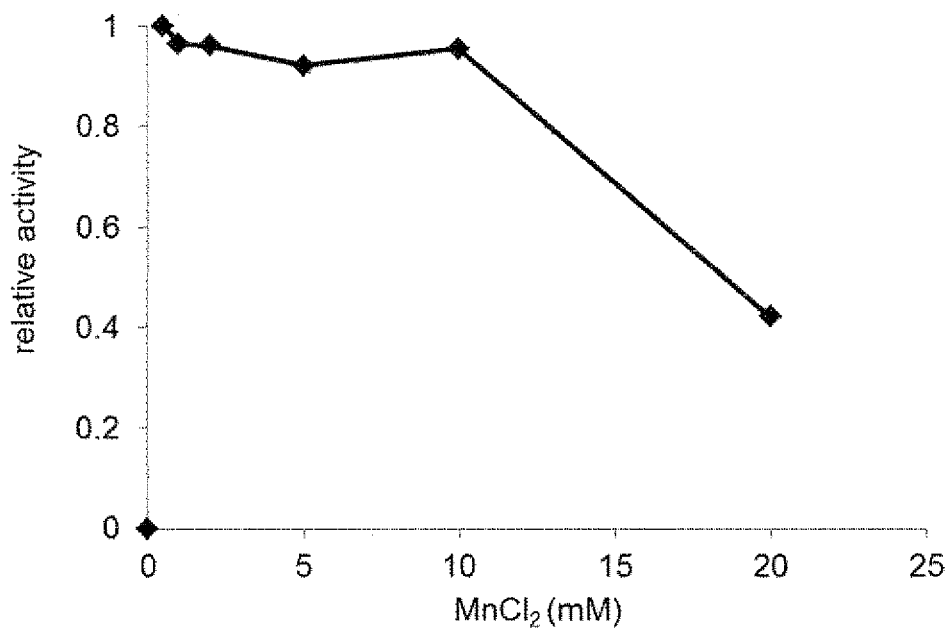
[Fig. 8]
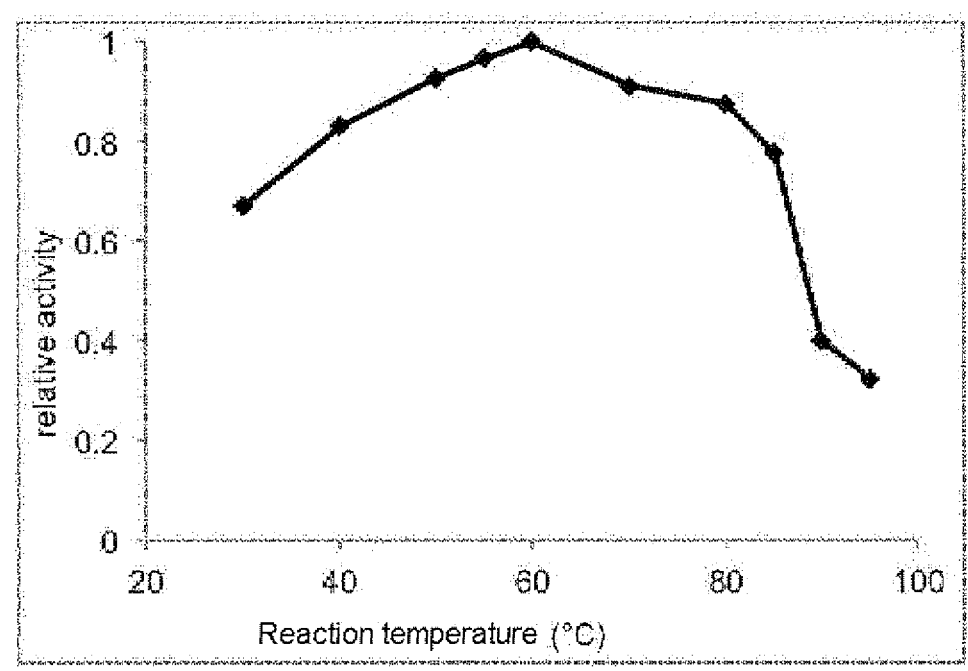

[Fig. 9]
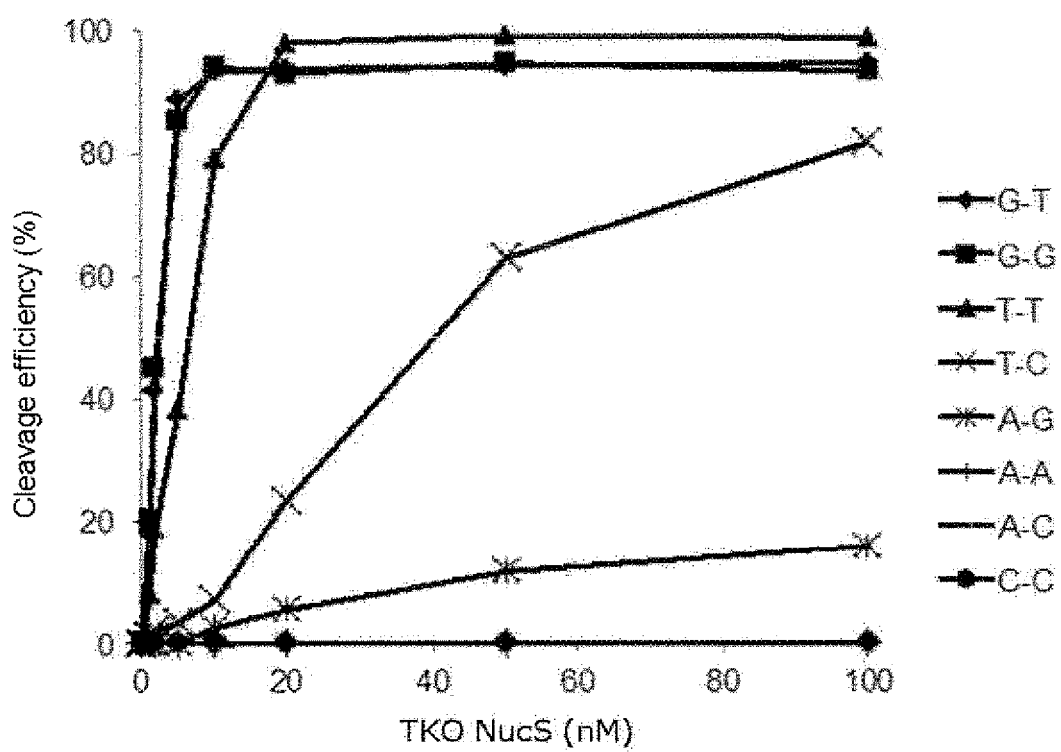

[Fig. 10]
all match (15bp) dsDNA (Cy5-15binding + 15binding_AT)
A-A (15bp) dsDNA (Cy5-15binding + 15binding_AA)
A-C (15bp) dsDNA (Cy5-15binding + 15binding_CA)
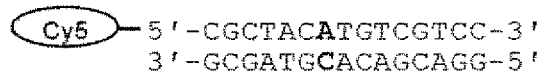
A-G (15bp) dsDNA (Cy5-15binding + 15binding_GA)
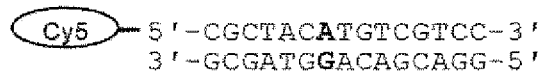
G-T (15bp) dsDNA (Cy5-15binding + 15binding_GT)
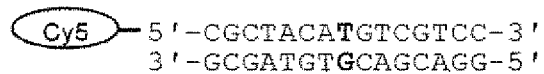
G-G (15bp) dsDNA (Cy5-15binding + 15binding_GG)
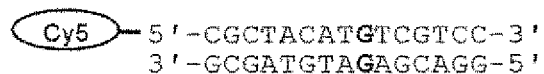
T-C (15bp) dsDNA (Cy5-15binding + 15binding_CT)
T-T (15bp) dsDNA (Cy5-15binding + 15binding_TT)
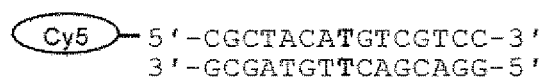
C-C (15bp) dsDNA (Cy5-15binding + 15binding_CC)
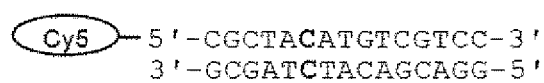

[Fig. 11]
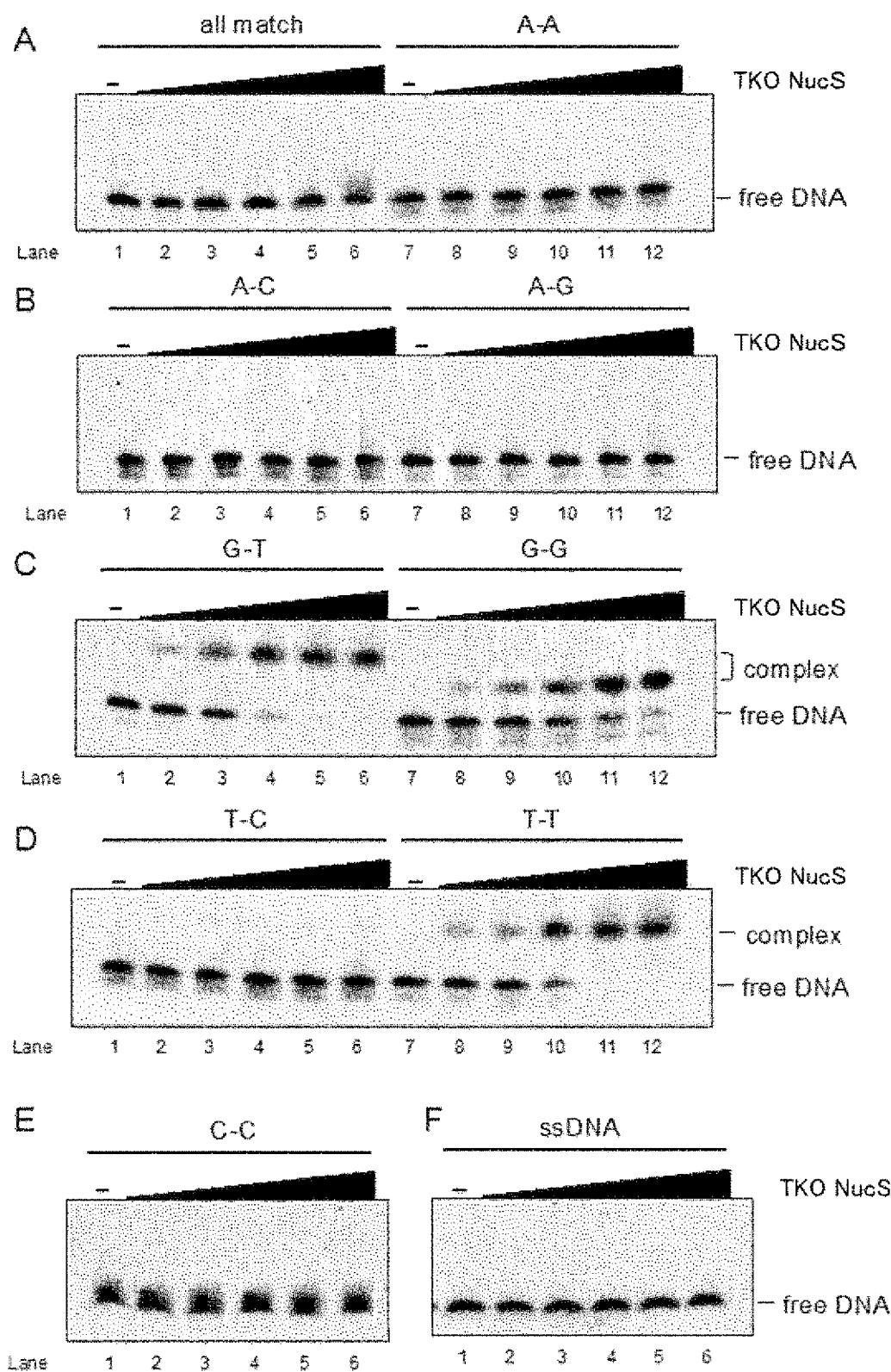

[Fig. 12]
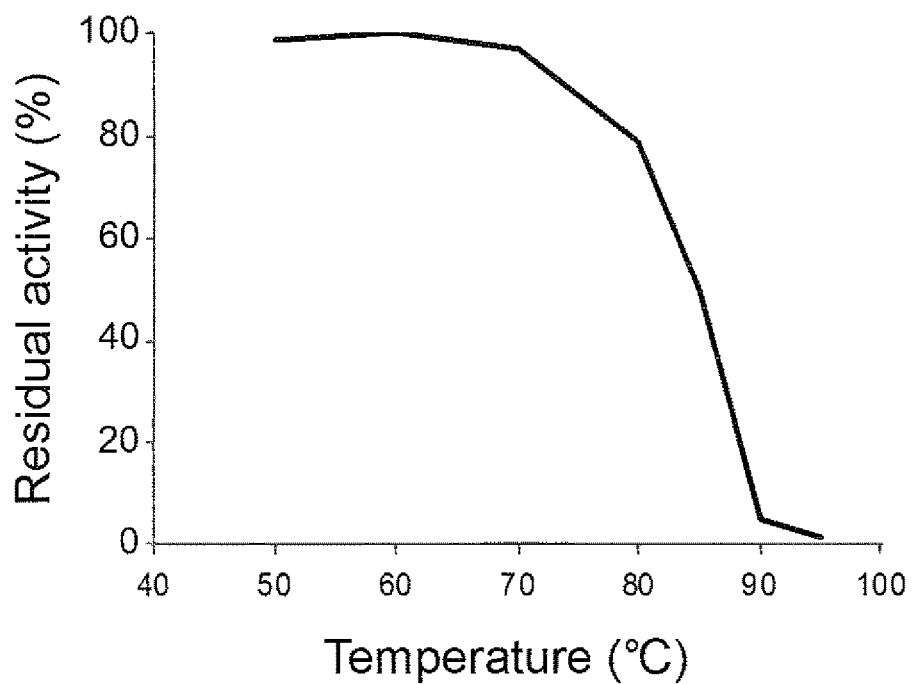

[Fig. 13]
A
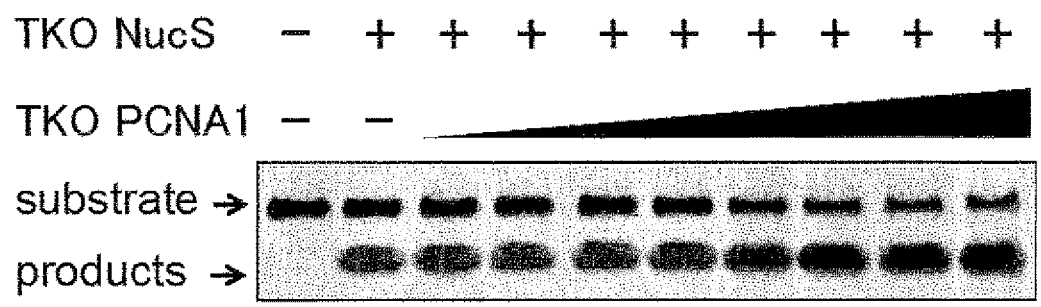
B
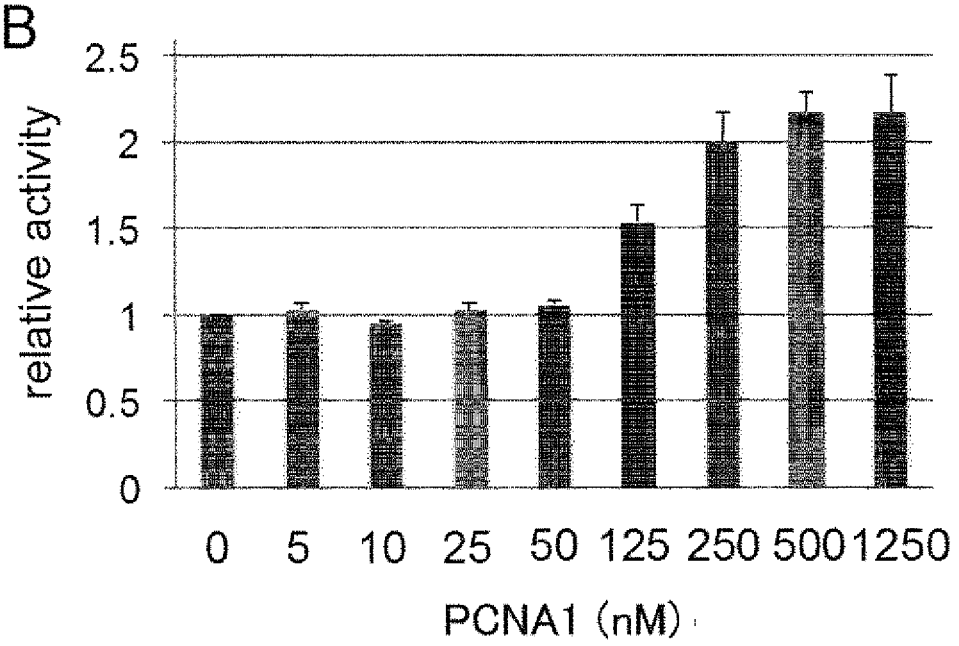

[Fig. 14]
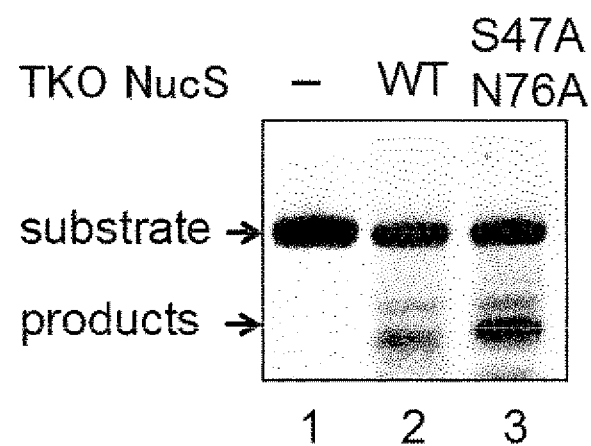

SEQUENCE LISTING

<160> NUMBER OF SEQ ID NOS: 30

<210> SEQ ID NO 1
<211> LENGTH: 252
<212> TYPE: PRT
<213> ORGANISM: Thermococcus kodakarensis

<400> SEQUENCE: 1

```
Met Ser Lys Asp Lys Val Thr Val Ile Thr Ser Pro Ser Thr Glu Glu
 1               5                  10                  15

Leu Val Ser Leu Val Asn Ser Ala Leu Leu Glu Glu Ala Met Leu Thr
            20                  25                  30

Ile Phe Ala Arg Cys Lys Val His Tyr Asp Gly Arg Ala Lys Ser Glu
        35                  40                  45

Leu Gly Ser Gly Asp Arg Val Ile Val Lys Pro Asp Gly Ser Phe
50                  55                  60

Leu Ile His Gln Ser Lys Lys Arg Glu Pro Val Asn Trp Gln Pro Pro
65                  70                  75                  80

Gly Ser Arg Val Arg Leu Glu Leu Arg Glu Asn Pro Val Leu Val Ser
                85                  90                  95

Ile Arg Arg Lys Pro Arg Glu Thr Leu Glu Val Glu Leu Glu Val
            100                 105                 110

Tyr Met Val Ser Val Phe Arg Ala Glu Asp Tyr Glu Glu Leu Ala Leu
            115                 120                 125

Thr Gly Ser Glu Ala Glu Met Ala Glu Leu Ile Phe Glu Asn Pro Glu
        130                 135                 140

Val Ile Glu Pro Gly Phe Lys Pro Leu Phe Arg Glu Lys Ala Ile Gly
145                 150                 155                 160

Thr Gly Ile Val Asp Val Leu Gly Arg Asp Ser Asp Gly Asn Ile Val
                165                 170                 175

Val Leu Glu Leu Lys Arg Arg Arg Ala Glu Leu His Ala Val Arg Gln
            180                 185                 190

Leu Lys Ser Tyr Val Glu Ile Leu Arg Glu Glu Tyr Gly Asp Lys Val
        195                 200                 205

Arg Gly Ile Leu Val Ala Pro Ser Leu Thr Ser Gly Ala Lys Arg Leu
    210                 215                 220

Leu Glu Lys Glu Gly Leu Glu Phe Arg Lys Leu Glu Pro Pro Lys Arg
225                 230                 235                 240

Asp Ser Lys Lys Lys Gly Arg Gln Lys Thr Leu Phe
                245                 250
```

<210> SEQ ID NO 2
<211> LENGTH: 759
<212> TYPE: DNA
<213> ORGANISM: Thermococcus kodakarensis

<400> SEQUENCE: 2

```
atgtccaagg ataaggtaac ggtcatcacg tcgccatcaa ccgaagaact cgtttcgcta      60
gtcaattcag ctctcttaga agaggccatg ctgacgattt ttgcccgctg taaggtccac     120
tacgatggaa gggcaaagag cgagctcggc tccggcgata gggtcatcat agtcaagccc     180
gacggctctt ttctcatcca ccagagcaag aagcgcgagc ccgtgaactg gcagccaccg     240
ggtagcagag tgaggctgga gctgagggag aacccagttc tcgtctcgat aaggagaaag     300
ccgagggaga cccttgaggt cgagctcgaa gaggtctaca tggtctccgt cttccgagct     360
gaggactacg aggagctcgc ccttacgggg agcgaggccg agatggcgga gcttatcttt     420
```

```
gaaaatccag aggtcataga gcctggcttc aagccgctgt tcagggagaa ggcgatagga    480
actggaatcg ttgatgtcct tggaagggac agtgatggga atatagttgt ccttgagctt    540
aagcgcagga gggcggaact ccatgccgtt agacagctca agagctacgt cgagattctg    600
agagaggagt acggcgataa agtccgtgga attctcgttg ctccctcgct cacttctggg    660
gcaaaaagac tcctggaaaa ggagggcctc gagttcagga agctcgaacc gcctaaaaga    720
gactccaaaa agaagggcag acagaagaca ctgttttag                           759
```

<210> SEQ ID NO 3
<211> LENGTH: 252
<212> TYPE: PRT
<213> ORGANISM: Thermococcus kodakarensis

<400> SEQUENCE: 3

```
Met Ser Lys Asp Lys Val Thr Val Ile Thr Ser Pro Ser Thr Glu Glu
1               5                   10                  15

Leu Val Ser Leu Val Asn Ser Ala Leu Leu Glu Glu Ala Met Leu Thr
            20                  25                  30

Ile Phe Ala Arg Cys Lys Val His Tyr Asp Gly Arg Ala Lys Ala Glu
        35                  40                  45

Leu Gly Ser Gly Asp Arg Val Ile Val Lys Pro Asp Gly Ser Phe
    50                  55                  60

Leu Ile His Gln Ser Lys Lys Arg Glu Pro Val Ala Trp Gln Pro Pro
65                  70                  75                  80

Gly Ser Arg Val Arg Leu Glu Leu Arg Glu Asn Pro Val Leu Val Ser
                85                  90                  95

Ile Arg Arg Lys Pro Arg Glu Thr Leu Glu Val Glu Leu Glu Glu Val
            100                 105                 110

Tyr Met Val Ser Val Phe Arg Ala Glu Asp Tyr Glu Glu Leu Ala Leu
        115                 120                 125

Thr Gly Ser Glu Ala Glu Met Ala Glu Leu Ile Phe Glu Asn Pro Glu
    130                 135                 140

Val Ile Glu Pro Gly Phe Lys Pro Leu Phe Arg Glu Lys Ala Ile Gly
145                 150                 155                 160

Thr Gly Ile Val Asp Val Leu Gly Arg Asp Ser Asp Gly Asn Ile Val
                165                 170                 175

Val Leu Glu Leu Lys Arg Arg Ala Glu Leu His Ala Val Arg Gln
            180                 185                 190

Leu Lys Ser Tyr Val Glu Ile Leu Arg Glu Glu Tyr Gly Asp Lys Val
        195                 200                 205

Arg Gly Ile Leu Val Ala Pro Ser Leu Thr Ser Gly Ala Lys Arg Leu
    210                 215                 220

Leu Glu Lys Glu Gly Leu Glu Phe Arg Lys Leu Glu Pro Pro Lys Arg
225                 230                 235                 240

Asp Ser Lys Lys Lys Gly Arg Gln Lys Thr Leu Phe
                245                 250
```

<210> SEQ ID NO 4
<211> LENGTH: 759
<212> TYPE: DNA
<213> ORGANISM: Thermococcus kodakarensis

<400> SEQUENCE: 4

```
atgtccaagg ataaggtaac ggtcatcacg tcgccatcaa ccgaagaact cgtttcgcta     60
gtcaattcag ctctcttaga agaggccatg ctgacgattt ttgcccgctg taaggtccac   120
```

```
tacgatggaa gggcaaaggc cgagctcggc tccggcgata gggtcatcat agtcaagccc      180
gacggctctt ttctcatcca ccagagcaag aagcgcgagc ccgtggcctg gcagccaccg      240
ggtagcagag tgaggctgga gctgagggag aacccagttc tcgtctcgat aaggagaaag      300
ccgagggaga cccttgaggt cgagctcgaa gaggtctaca tggtctccgt cttccgagct      360
gaggactacg aggagctcgc ccttacgggg agcgaggccg agatggcgga gcttatcttt      420
gaaaatccag aggtcataga gcctggcttc aagccgctgt tcaggagaa ggcgatagga       480 actggaatcg ttgatgtcct tggaagggac agtgatggga atatagttgt ccttgagctt      540
aagcgcagga gggcggaact ccatgccgtt agacagctca agagctacgt cgagattctg      600
agagaggagt acggcgataa agtccgtgga attctcgttg ctccctcgct cacttctggg      660
gcaaaaagac tcctggaaaa ggagggcctc gagttcagga agctcgaacc gcctaaaaga      720
gactccaaaa agaagggcag acagaagaca ctgttttag                            759
```

<210> SEQ ID NO 5
<211> LENGTH: 34
<212> TYPE: DNA
<213> ORGANISM: Artificial Sequence
<220> FEATURE:
<223> OTHER INFORMATION: TK1898-F primer

<400> SEQUENCE: 5

```
cgcgcatatg tccaaggata aggtaacggt catc                                  34
```

<210> SEQ ID NO 6
<211> LENGTH: 39
<212> TYPE: DNA
<213> ORGANISM: Artificial Sequence
<220> FEATURE:
<223> OTHER INFORMATION: TK1898-R primer

<400> SEQUENCE: 6

```
ggggcggccg ctcaaaacag tgtcttctgt ctgcccttc                             39
```

<210> SEQ ID NO 7
<211> LENGTH: 45
<212> TYPE: DNA
<213> ORGANISM: Artificial Sequence
<220> FEATURE:
<223> OTHER INFORMATION: Substrate for TKO NucS, named as
      Cy5-45-nondamaged. "5'-end is labeled with Cy5"

<400> SEQUENCE: 7

```
cgaactgcct ggaatcctga cgacatgtag cgaacgatca cctca                      45
```

<210> SEQ ID NO 8
<211> LENGTH: 45
<212> TYPE: DNA
<213> ORGANISM: Artificial Sequence
<220> FEATURE:
<223> OTHER INFORMATION: Substrate for TKO NucS, named as
      Cy5-45-mismatch. "5'-end is labeled with Cy5"

<400> SEQUENCE: 8

```
cgaactgcct ggaatcctga cgacgtgtag cgaacgatca cctca                      45
```

<210> SEQ ID NO 9
<211> LENGTH: 45
<212> TYPE: DNA
<213> ORGANISM: Artificial Sequence

```
<220> FEATURE:
<223> OTHER INFORMATION: Substrate for TKO NucS, named as Cy5-temp45.
      "5'-end is labeled with Cy5"

<400> SEQUENCE: 9
tgaggtgatc gttcgctaca tgtcgtcagg attccaggca gttcg                45

<210> SEQ ID NO 10
<211> LENGTH: 45
<212> TYPE: DNA
<213> ORGANISM: Artificial Sequence
<220> FEATURE:
<223> OTHER INFORMATION: Substrate for TKO NucS, named as temp45-normal.

<400> SEQUENCE: 10
tgaggtgatc gttcgctaca tgtcgtcagg attccaggca gttcg                45

<210> SEQ ID NO 11
<211> LENGTH: 45
<212> TYPE: DNA
<213> ORGANISM: Artificial Sequence
<220> FEATURE:
<223> OTHER INFORMATION: Substrate for TKO NucS, named as temp45-21A.

<400> SEQUENCE: 11
tgaggtgatc gttcgctaca agtcgtcagg attccaggca gttcg                45

<210> SEQ ID NO 12
<211> LENGTH: 45
<212> TYPE: DNA
<213> ORGANISM: Artificial Sequence
<220> FEATURE:
<223> OTHER INFORMATION: Substrate for TKO NucS, named as  temp45-21C.

<400> SEQUENCE: 12
tgaggtgatc gttcgctaca cgtcgtcagg attccaggca gttcg                45

<210> SEQ ID NO 13
<211> LENGTH: 45
<212> TYPE: DNA
<213> ORGANISM: Artificial Sequence
<220> FEATURE:
<223> OTHER INFORMATION: Substrate for TKO NucS, named as  temp45-21G.

<400> SEQUENCE: 13
tgaggtgatc gttcgctaca ggtcgtcagg attccaggca gttcg                45

<210> SEQ ID NO 14
<211> LENGTH: 45
<212> TYPE: DNA
<213> ORGANISM: Artificial Sequence
<220> FEATURE:
<223> OTHER INFORMATION: Substrate for TKO NucS, named as
      45-mismatch25C.

<400> SEQUENCE: 14
cgaactgcct ggaatcctga cgacctgtag cgaacgatca cctca                45

<210> SEQ ID NO 15
<211> LENGTH: 45
<212> TYPE: DNA
<213> ORGANISM: Artificial Sequence
<220> FEATURE:
<223> OTHER INFORMATION: Substrate for TKO NucS, named as
      45-mismatch25T.
```

<400> SEQUENCE: 15
cgaactgcct ggaatcctga cgacttgtag cgaacgatca cctca    45

<210> SEQ ID NO 16
<211> LENGTH: 45
<212> TYPE: DNA
<213> ORGANISM: Artificial Sequence
<220> FEATURE:
<223> OTHER INFORMATION: Substrate for TKO NucS, named as
      nondamaged-22C.

<400> SEQUENCE: 16
cgaactgcct ggaatcctga ccacatgtag cgaacgatca cctca    45

<210> SEQ ID NO 17
<211> LENGTH: 15
<212> TYPE: DNA
<213> ORGANISM: Artificial Sequence
<220> FEATURE:
<223> OTHER INFORMATION: Substrate for TKO NucS, named as Cy5-15binding.
      "5'-end is labeled with Cy5"

<400> SEQUENCE: 17
cgctacatgt cgtcc    15

<210> SEQ ID NO 18
<211> LENGTH: 15
<212> TYPE: DNA
<213> ORGANISM: Artificial Sequence
<220> FEATURE:
<223> OTHER INFORMATION: Substrate for TKO NucS, named as 15binding_AT.

<400> SEQUENCE: 18
ggacgacatg tagcg    15

<210> SEQ ID NO 19
<211> LENGTH: 15
<212> TYPE: DNA
<213> ORGANISM: Artificial Sequence
<220> FEATURE:
<223> OTHER INFORMATION: Substrate for TKO NucS, named as 15binding_AA.

<400> SEQUENCE: 19
ggacgacaag tagcg    15

<210> SEQ ID NO 20
<211> LENGTH: 15
<212> TYPE: DNA
<213> ORGANISM: Artificial Sequence
<220> FEATURE:
<223> OTHER INFORMATION: Substrate for TKO NucS, named as 15binding_CA.

<400> SEQUENCE: 20
ggacgacacg tagcg    15

<210> SEQ ID NO 21
<211> LENGTH: 15
<212> TYPE: DNA
<213> ORGANISM: Artificial Sequence
<220> FEATURE:
<223> OTHER INFORMATION: Substrate for TKO NucS, named as 15binding_GA.

<400> SEQUENCE: 21
ggacgacagg tagcg    15

```
<210> SEQ ID NO 22
<211> LENGTH: 15
<212> TYPE: DNA
<213> ORGANISM: Artificial Sequence
<220> FEATURE:
<223> OTHER INFORMATION: Substrate for TKO NucS, named as 15binding_GT.

<400> SEQUENCE: 22
ggacgacgtg tagcg                                                         15

<210> SEQ ID NO 23
<211> LENGTH: 15
<212> TYPE: DNA
<213> ORGANISM: Artificial Sequence
<220> FEATURE:
<223> OTHER INFORMATION: Substrate for TKO NucS, named as 15binding_GG.

<400> SEQUENCE: 23
ggacgagatg tagcg                                                         15

<210> SEQ ID NO 24
<211> LENGTH: 15
<212> TYPE: DNA
<213> ORGANISM: Artificial Sequence
<220> FEATURE:
<223> OTHER INFORMATION: Substrate for TKO NucS, named as 15binding_CT.

<400> SEQUENCE: 24
ggacgacctg tagcg                                                         15

<210> SEQ ID NO 25
<211> LENGTH: 15
<212> TYPE: DNA
<213> ORGANISM: Artificial Sequence
<220> FEATURE:
<223> OTHER INFORMATION: Substrate for TKO NucS, named as 15binding_TT.

<400> SEQUENCE: 25
ggacgacttg tagcg                                                         15

<210> SEQ ID NO 26
<211> LENGTH: 15
<212> TYPE: DNA
<213> ORGANISM: Artificial Sequence
<220> FEATURE:
<223> OTHER INFORMATION: Substrate for TKO NucS, named as 15binding_CC.

<400> SEQUENCE: 26
ggacgacatc tagcg                                                         15

<210> SEQ ID NO 27
<211> LENGTH: 33
<212> TYPE: DNA
<213> ORGANISM: Artificial Sequence
<220> FEATURE:
<223> OTHER INFORMATION: A47-F primer

<400> SEQUENCE: 27
cgatggaagg gcaaaggccg agctcggctc cgg                                     33

<210> SEQ ID NO 28
<211> LENGTH: 33
<212> TYPE: DNA
<213> ORGANISM: Artificial Sequence
```

```
<220> FEATURE:
<223> OTHER INFORMATION: A47-R primer

<400> SEQUENCE: 28
ccggagccga gctcggcctt tgcccttcca tcg                              33

<210> SEQ ID NO 29
<211> LENGTH: 33
<212> TYPE: DNA
<213> ORGANISM: Artificial Sequence
<220> FEATURE:
<223> OTHER INFORMATION: A76-F primer

<400> SEQUENCE: 29
gaagcgcgag cccgtggcct ggcagccacc ggg                              33

<210> SEQ ID NO 30
<211> LENGTH: 33
<212> TYPE: DNA
<213> ORGANISM: Artificial Sequence
<220> FEATURE:
<223> OTHER INFORMATION: A76-R primer

<400> SEQUENCE: 30
cccggtggct gccaggccac gggctcgcgc ttc                              33
```

METHODS OF UTILIZING THERMOSTABLE MISMATCH ENDONUCLEASE

TECHNICAL FIELD

The present invention relates to a novel heat-resistant mismatch endonuclease which recognizes and cleaves a mismatched base pair in a double-stranded nucleic acid, a composition comprising the mismatch endonuclease, and a method of using the mismatch endonuclease.

BACKGROUND ART

In recent years, mutation analysis methods have been remarkably developed. The mutation analysis methods have been used for genetic diagnoses of human beings as well as improvement of agricultural crops and isolation or creation of useful microorganisms, and thus have greatly contributed to general living.

Many mutation analysis methods comprise direct analyses of genomic sequences. However, there are some mutation analysis methods comprising use of enzymes that recognize mismatched base pairs. A mutation analysis method comprises detection with a factor capable of binding specifically to a mismatched base pair formed from mutant-type DNA and a wild-type DNA. A representative example of the mutation analysis method comprises detection of mutation sites by use of MutS, MutT, and MutL complexes from *Escherichia coli* (Patent Literature 1).

A mutation analysis method comprising use of a mismatch endonuclease which specifically cleaves mismatch sites is also known. In such a method, a mismatch endonuclease is used to cleave a DNA in the vicinity of a mismatched base pair, and the DNA fragments thus obtained are analyzed to detect the presence or absence and the position of mutations.

As a representative example, a method comprising use of a Cell gene product from celery is known (Patent Literature 2), and the method is actually used for analyses of base mutations. However, the enzyme is not heat-resistant, and therefore cannot be used in techniques involving a high-temperature reaction process, such as PCR. Thus, in order to detect base mutations, the method requires four steps of amplification, formation of mismatches, cleavage of mismatches, and detection.

In recent years, heat-resistant mismatch endonucleases have been developed, and their uses have been expected. The mismatch endonucleases are characterized by recognizing G-G, G-T, T-G, and T-T mismatch sites and cleaving both chains of DNA in the vicinity of the mismatches (Patent Literature 3).

In addition to mutation analysis, examples of biotechnological techniques that have a lot of influence include nucleic acid amplification techniques.

A representative example of the nucleic acid amplification techniques is polymerase chain reaction (PCR). PCR is a technique for easily amplifying a desired fragment of a nucleic acid in vitro. PCR is an experimental technique, which is essential in broad fields including the fields of biology, medicine, and agriculture, as well as research regarding genes. PCR is also applied to detection of mutated genes and analysis of methylation of DNA.

Isothermal nucleic acid amplification methods such as a LAMP method and an ICAN method do not require special equipment, and therefore, they are used as cheaper methods for detection of nucleic acids.

For structural analyses of the whole genome, which have been performed in recent years, a whole-genome amplification method is an important technique, in particular, for analysis of scarce samples.

In these nucleic acid amplification methods, incorporation of incorrect bases occurs with a constant probability. The probability has been reduced through improvement of DNA polymerases or the like. However, the incorporation of incorrect bases still disturbs precise analysis.

In constructing genomic libraries or cDNA libraries, the nucleic acid amplification methods preferentially amplify a DNA molecule with a higher content, which may disturb analysis or screening of various kinds of DNAs.

To solve the above problem, the proportion of a DNA with a higher content is reduced by normalization utilizing self-hybridization (Non-patent Literature 1). SSH-PCR in which PCP and self-hybridization are combined is also used (Non-patent Literature 2). Using these methods, however, DNAs homologous to the DNA with a higher content may be also removed.

In detection of a DNA by a nucleic acid amplification method, a target DNA and a non-target DNA may compete for amplification. In other words, when a non-target DNA is amplified simultaneously with amplification of a target DNA, it is difficult to detect the target DNA. The above problem may be solved by use of real-time PCR in which probes such as cycling probes or TaqMan probes are used to detect only a target DNA. In the case where a non-target DNA exists in an excessively large amount relative to a target DNA, however, it is difficult to precisely detect the target DNA because of false-positive reaction with many similar DNAs.

Such a problem may occur in detection of a small number of mutant alleles in the presence of normal alleles (for example, detection of circulating tumor DNA), detection of a small number of methylated or non-methylated alleles by epigenetic assay, detection of a small amount of fetal DNA sequences circulating in the mother's blood, and the like.

To solve the above problem, a method termed restriction endonuclease-mediated selective polymerase chain reaction (REMS PCR) has been developed (Non-patent Literature 3). This method involves use of a heat-resistant restriction enzyme. In this method, a DNA having a mutant nucleotide sequence is selectively detected using primers which, for example, are designed so that cleavage by the restriction enzyme occurs only when a template has a normal nucleotide sequence. Depending on a target DNA to be detected, however, there may be no heat-resistant restriction enzyme having a recognition sequence suitable to selective detection by REMS PCR. Thus REMS PCR lacks versatility.

As described above, regard to the mutation detection method involving nucleic acid amplification, there is a need for a method of avoiding false-positive reaction with many similar DNAs even when a non-target DNA exists in an excessively large amount relative to a target DNA.

CITATION LIST

Patent Literature

Patent Literature 1: U.S. Pat. No. 5,922,539 B
Patent Literature 2: WO 01/062974
Patent Literature 3: WO 2014/142261

Non Patent Literature

Non-Patent Literature 1: "Nucleic Acids Research", 2004 February, vol. 32, NO:3, e37

Non-Patent Literature 2: "Methods in Molecular Biology", *DNA and RNA Profiling in Human Blood: Methods and Protocols,* 2009, vol. 496, pp. 223-243

Non-Patent Literature 3: "American Journal of Pathology", 1998 August, vol. 153, No. 2, pp. 373-379

SUMMARY OF INVENTION

Technical Problems

Objectives of the present invention include provision of a novel mismatch endonuclease, a composition comprising the mismatch endonuclease, and a use of the mismatch endonuclease.

Solution to Problems

As a result of intensive efforts under the above circumstances, the present inventors have found that a polypeptide from *Thermococci kodakarensis*, which has been regarded as a factor in the replication mechanism, has a heat-resistant mismatch endonuclease activity. Hereinafter, the polypeptide having the enzymatic activity is referred to as TKO NucS.

Furthermore, the present inventors have successfully created a mutant of the heat-resistant mismatch endonuclease, which has increased base-specificity different from the base-specificity of the wild-type mismatch endonuclease. The present inventors have found that when the mutant-type mismatch endonuclease and/or the wild-type mismatch endonuclease are used alone or in combination, cleavage of base pairs other than a specific mismatched base pair is inhibited, allowing more specific inhibition of amplification. Thus the present invention has been completed.

Specifically, the first aspect of the present invention relates to a method of cleaving a double-stranded nucleic acid, comprising treating a double-stranded nucleic acid having a mismatched base pair with at least one polypeptide selected from the group consisting of the following (i) to (iii) to recognize and cleave both strands of the double-stranded nucleic acid at the position of a G-G, G-T, or T-T mismatched base pair:

(i) a polypeptide having an amino acid sequence of SEQ ID NO:1;

(ii) a polypeptide having an amino acid sequence which differs from the amino acid sequence of SEQ ID NO:1 by substitution, deletion, insertion and/or addition of 1 to several amino acid residues, and having a mismatch endonuclease activity which recognizes and cleaves a G-G, G-T, or T-T mismatch; and (iii) a polypeptide having an amino acid sequence which shares at least 95% amino acid sequence identity with the amino acid sequence of SEQ ID NO:1, and having a mismatch endonuclease activity which recognizes and cleaves a G-G, G-T, or T-T mismatch.

The second aspect of the present invention relates to a composition comprising the following (a) to (c):

(a) a DNA polymerase;

(b) at least one pair of oligonucleotide primers; and (c) at least one polypeptide selected from the group consisting of the following (i) to (iii):

(i) a polypeptide having an amino acid sequence of SEQ ID NO:1;

(ii) a polypeptide having an amino acid sequence which differs from the amino acid sequence of SEQ ID NO:1 by substitution, deletion, insertion and/or addition of 1 to several amino acid residues, and having a mismatch endonuclease activity which recognizes and cleaves a G-G, G-T, or T-T mismatch; and (iii) a polypeptide having an amino acid sequence which shares at least 95% amino acid sequence identity with the amino acid sequence of SEQ ID NO:1, and having a mismatch endonuclease activity which recognizes and cleaves a G-G, G-T, or T-T mismatch.

The third aspect of the present invention relates to a method of amplifying a nucleic acid, comprising the following steps (a) and (b):

(a) preparing a composition comprising the composition according to the second aspect of the present invention and a nucleic acid molecule as a template; and (b) reacting the composition obtained by step (a) under suitable conditions to perform nucleic acid amplification.

The fourth aspect of the present invention relates to a polypeptide selected from the group consisting of the following (A) to (C):

(A) a polypeptide having an amino acid sequence of SEQ ID NO:3;

(B) a polypeptide having an amino acid sequence which differs from the amino acid sequence of the polypeptide of (A) by substitution, deletion, insertion and/or addition of 1 to several amino acid residues other than amino acid residues at positions 47 and 76, and having a mismatch endonuclease activity which recognizes and cleaves a A-A, A-C, or C-C mismatch; and (C) a polypeptide having an amino acid sequence which shares at least 90% amino acid sequence identity with the amino acid sequence of SEQ ID NO:3, in which amino acid residues corresponding to serine at position 47 and asparagine at position 76 in the amino acid sequence of SEQ ID NO:1 are substituted with other amino acid residues, and having a mismatch endonuclease activity which recognizes and cleaves a A-A, A-C, or C-C mismatch.

The fifth aspect of the present invention relates to a composition comprising the following (a) to (c):

(a) a DNA polymerase;

(b) at least one pair of oligonucleotide primers; and (c) at least one polypeptide selected from the group consisting of the following (i) to (iii):

(i) a polypeptide having an amino acid sequence of SEQ ID NO:3;

(ii) a polypeptide having an amino acid sequence which differs from the amino acid sequence of the polypeptide of (i) by substitution, deletion, insertion and/or addition of 1 to several amino acid residues other than amino acid residues at positions 47 and 76, and having a mismatch endonuclease activity which recognizes and cleaves a A-A, A-C, or C-C mismatch; and (iii) a polypeptide having an amino acid sequence which shares at least 90% amino acid sequence identity with the amino acid sequence of SEQ ID NO:3, in which amino acid residues corresponding to serine at position 47 and asparagine at position 76 in the amino acid sequence of SEQ ID NO:1 are substituted with other amino acid residues, and having a mismatch endonuclease activity which recognizes and cleaves a A-A, A-C, or C-C mismatch.

The sixth aspect of the present invention relates to a method of amplifying a nucleic acid, comprising the following steps (a) and (b):

(a) preparing a composition comprising the composition according to the fifth aspect of the present invention and a nucleic acid molecule as a template; and (b) reacting the composition obtained by step (a) under suitable conditions to perform nucleic acid amplification.

The seventh aspect of the present invention relates to a method of inhibiting amplification of a nucleic acid having a specific nucleotide sequence in a nucleic acid amplification reaction, comprising a step of performing the nucleic acid amplification reaction in the presence of the following (a) to (d):

(a) an oligodeoxyribonucleotide which is designed to generate one to several mismatches when the oligodeoxyribonucleotide is hybridized with the nucleic acid having a specific nucleotide sequence or a complementary strand thereof;

(b) a DNA polymerase;

(c) at least one pair of oligonucleotide primers; and (d) the polypeptide used in the first aspect of the present invention and/or the polypeptide according to the fourth aspect of the present invention.

The mismatch endonuclease used in the method according to the seventh aspect of the present invention may be replaced by another heat-resistant microorganism-derived polypeptide having a mismatch endonuclease activity equivalent to the polypeptide used in the first aspect of the present invention or the polypeptide according to the fourth aspect of the present invention.

The eighth aspect of the present invention relates to a method of preferentially amplifying a target nucleic acid, comprising inhibiting amplification of a nucleic acid having a nucleotide sequence different from that of the target nucleic acid in one to several nucleotides by the method according to the seventh aspect of the present invention.

In the method according to the eighth aspect of the present invention, the amplification may be performed in the presence of a proliferating cell nuclear antigen (PCNA) derived from a heat-resistant microorganism or a homolog thereof.

The ninth aspect of the present invention relates to a method of detecting a mutation in a target nucleic acid, comprising using the polypeptide used in the method according to the first aspect of the present invention and/or the polypeptide according to the fourth aspect of the present invention. The mismatch endonuclease used in the method according to the ninth aspect of the present invention may be replaced by another heat-resistant microorganism-derived polypeptide having a mismatch endonuclease activity equivalent to the polypeptide used in the first aspect of the present invention or the polypeptide according to the fourth aspect of the present invention.

Effects of the Invention

According to the present invention, a mismatch endonuclease which has great utility in biotechnology and which recognizes a different mismatch sequence, a composition comprising the mismatch endonuclease, and a method of using the mismatch endonuclease are provided.

BRIEF DESCRIPTION OF DRAWINGS

FIG. 1 shows a result of SDS-PAGE showing purification of the mismatch endonuclease of the present invention.

FIG. 2 provides a list of substrate DNAs used in measurement of the activity of the mismatch endonuclease of the present invention.

FIG. 3 shows results of Native-PAGE and a graph showing the mismatch DNA cleavage activity of the mismatch endonuclease of the present invention.

FIG. 4 provides a graph showing effects of pH on mismatch DNA cleavage reaction by the mismatch endonuclease of the present invention.

FIG. 5 provides graphs showing effects of sodium chloride, potassium chloride, and potassium glutamate on mismatch DNA cleavage reaction by the mismatch endonuclease of the present invention.

FIG. 6 provides graphs showing effect's of magnesium chloride on mismatch DNA cleavage reaction by the mismatch endonuclease of the present invention.

FIG. 7 provides a graph showing effects of manganese chloride on mismatch DNA cleavage reaction by the mismatch endonuclease of the present invention.

FIG. 8 provides a graph showing effects of temperature on mismatch DNA cleavage reaction by the mismatch endonuclease of the present invention.

FIG. 9 provides a graph showing the cleavage activities of the mismatch endonuclease of the present invention against various mismatch DNAs.

FIG. 10 provides a list of probe DNAs used in measurement of the DNA-binding activity of the mismatch endonuclease of the present invention.

FIG. 11 shows results of Native-PAGE showing measurement of the DNA-binding activity of the mismatch endonuclease of the present invention.

FIG. 12 provides a graph showing the heat-resistance of the mismatch endonuclease of the present invention.

FIG. 13 shows results of Native-PAGE and a graph showing the mismatched DNA-cleavage activity of the mismatch endonuclease of the present invention in the presence of PCNA1 from TKO.

FIG. 14 shows results of Native-PAGE showing the cleavage activity of the mismatch endonuclease of the present invention against A-A mismatch DNA.

DESCRIPTION OF EMBODIMENTS

Hereinafter, the present invention is explained in detail.

In the present invention, the word "mismatch" refers to base pairings different from Watson-Crick base pairs present in double-stranded nucleic acids, in other words, binding of bases in combinations other than base pairings of G (guanine base)-C (cytosine base), and A (adenine base)-T (thymine base) or U (uracil base).

(1) Heat-Resistant Mismatch Endonuclease of the Present Invention and Mutants Thereof As used herein, "a polypeptide having a mismatch endonuclease activity (sometimes, referred to as a mismatch endonuclease)" means a nuclease having the activity of cleaving mismatch sites present in double-stranded nucleic acids. The mismatch endonuclease activity includes an activity of cleaving phosphodiester bonds adjacent to nucleotides forming mismatched base pairs, and an activity of cleaving phosphodiester bonds adjacent to nucleotides located 1 to 5, preferably 1 to 3 base pairs away from mismatched base pairs. In the present invention, the mismatch endonuclease is preferably a nuclease having the activity of specifically recognizing a specific mismatched base pair in a double-stranded nucleic acid to cleave the double-stranded nucleic acid. Examples of the mismatch endonuclease include endonucleases which recognize and cleave at least a G-G, G-T or T-T mismatch. The endonucleases may recognize and cleave only a G-G mismatch, only a G-T mismatch, or only a T-T mismatch. The endonucleases may recognize and cleave any two mismatches of a G-G mismatch, a G-T mismatch, and a T-T mismatch. The endonucleases may recognize and cleave all of a G-G mismatch, a G-T mismatch, and a T-T mismatch.

In the present invention, other mismatch endonucleases are further provided. Examples of the other mismatch endonucleases include endonucleases which specifically recognize and cleave an A-A, A-C or C-C mismatch. The endonucleases may recognize and cleave only an A-A mismatch, only an A-C mismatch, or only a C-C mismatch. The endonucleases may recognize and cleave any two mismatches of an A-A mismatch, an A-C mismatch, and a C-C mismatch. The endonucleases may recognize and cleave all of an A-A mismatch, an A-C mismatch, and a C-C mismatch.

The heat-resistant mismatch endonuclease may have, in addition to the activity of cleaving a mismatch site present in a double-stranded nucleic acid, the activity of recognizing a single-stranded DNA, a junction part between a single-stranded nucleic acid and a double-stranded nucleic acid, double flap structure, replication fork structure, D-loop structure, and/or Holliday junction structure with a nick to cleave the nucleic acid. As used herein, the heat-resistant mismatch endonuclease means a nuclease that exhibits the activity of cleaving a mismatch site in a double-stranded nucleic acid at temperature of 40° C. or higher, preferably 50° C. or higher, more preferably 60° C. or higher.

Examples of the heat-resistant mismatch endonuclease used in the present invention include, but not limited to, polypeptides having a heat-resistant mismatch endonuclease activity from *Thermococcus kodakarensis* (or *Thermococcus kodakaraensis*). The present inventors have found that a polypeptide from *Thermococcus kodakarensis* (SEQ ID NO:1) is a heat-resistant endonuclease which recognizes and cleaves a G-G, G-T or T-T mismatch. Furthermore, homologs of the polypeptide having an amino acid sequence shown by SEQ ID NO:1 are also suitable as the heat-resistant endonucleases in the present invention which recognizes and cleaves a G-G, G-T or T-T mismatch. Examples of the homologs include polypeptides having an amino acid sequence which differs from the amino acid sequence of SEQ ID NO:1 by substitution, deletion, insertion and/or addition of 1 to several amino acid residues, for example 1 to 15, preferably 1 to 9, more preferably 1 to 5, more preferably 1 to 3 amino acid residues; and polypeptides having an amino acid sequence which shares at least 95% amino acid sequence identity with the amino acid sequence of SEQ ID NO:1. Further, for example, the endonuclease having a nucleotide sequence shown by SEQ ID NO: 2 is preferably used.

Furthermore, the present inventors have found that a mutant-type polypeptide having an amino acid sequence which differs from the amino acid sequence of SEQ ID NO:1 by substitution of serine at position 47 and asparagine at position 76 with other amino acid residues, preferably by substitution of the residue at position 47 with alanine and substitution of the residue at position 76 with alanine, is a heat-resistant mismatch endonuclease that specifically recognizes an A-A, A-C, or C-C mismatch. Thus, an aspect of the present invention includes a polypeptide having an amino acid sequence of SEQ ID NO:3 thus created and homologs thereof. Examples of the homologs of the polypeptide having an amino acid sequence of SEQ ID NO:3 include a polypeptide having an amino acid sequence which differs from the amino acid sequence of SEQ ID NO:3 by substitution, deletion, insertion and/or addition of 1 to several amino acid residues, for example 1 to 15, preferably 1 to 9, more preferably 1 to 5, more preferably 1 to 3 amino acid residues other than the amino acid residues at position 47 and 76, and having an endonuclease activity which recognizes and cleaves an A-A, A-C, or C-C mismatch; a polypeptide having an amino acid sequence which differs from the amino acid sequence of SEQ ID NO:3 by substitution of alanine at position 47 and alanine at position 76 with other amino acid residues, and having an endonuclease activity which recognizes and cleaves an A-A, A-C, or C-C mismatch; a polypeptide having an amino acid sequence which differs from the amino acid sequence of the above-mentioned polypeptide by substitution, deletion, insertion and/or addition of 1 to several amino acid residues, for example 1 to 15, preferably 1 to 9, more preferably 1 to 5, more preferably 1 to 3 amino acid residues other than the amino acid residues at position 47 and 76, and having an endonuclease activity which recognizes and cleaves an A-A, A-C, or C-C mismatch; and a polypeptide having an amino acid sequence which shares at least 90%, preferably at least 95% amino acid sequence identity with the amino acid sequence of SEQ ID NO:3, in which an amino acid residue corresponding to alanine at position 47 in the amino acid sequence of SEQ ID NO:3 is an amino acid residue other than serine and an amino acid residue corresponding to alanine at position 76 in the amino acid sequence of SEQ ID NO:3 is an amino acid residue other than asparagine, and having an endonuclease activity which recognizes and cleaves an A-A, A-C, or C-C mismatch. Further, for example, the endonuclease having the nucleotide sequence of SEQ ID NO: 4 can be preferably used. Such mismatch endonucleases are suitable for various uses as described later, for example, a method comprising removing a DNA containing a specific DNA sequence and amplifying and detecting other DNAs.

In the present invention, the mismatch endonuclease activity can be measured by use of a double-stranded nucleic acid containing a mismatched base pair as a substrate. Specifically, after a double-stranded nucleic acid containing a mismatched base pair is prepared, the double-stranded nucleic acid is reacted with a mismatch endonuclease in which the amount of double-stranded nucleic acid is excess relative to the amount of the mismatch endonuclease, and then, the amount of nucleic acids cleaved per unit time is measured. The cleaved double-stranded nucleic acids can be quantified separately from non-cleaved nucleic acids, for example, by electrophoresis. A double-stranded nucleic acid double-labeled with a fluorescent substance and a quencher substance may be used so that an increase in fluorescent intensity can be detected only when the double-stranded nucleic acid is cleaved. Using such a double-stranded nucleic acid double-labeled with a fluorescent substance and a quencher substance, the mismatch endonuclease activity can be easily determined by measuring the fluorescent intensity in a reaction mixture at suitable time intervals. The cleavage activity on a specific mismatched base pair can be determined by changing bases forming a mismatched base pair present in a double-stranded nucleic acid used as a substrate.

(2) Cleavage Method of Double-Stranded Nucleic Acid by Use of Mismatch Endonuclease of the Present Invention The method of cleaving a double-stranded nucleic acid of the present invention comprises treating a double-stranded nucleic acid having a mismatched base pair with a polypeptide having the amino acid sequence of SEQ ID NO:1 or SEQ ID NO:3, or a homolog thereof. Examples of the homolog of the polypeptide having the amino acid sequence of SEQ ID NO:1 or SEQ ID NO:3 include, but not limited to, a polypeptide having an amino acid sequence which differs from the amino acid sequence of SEQ ID NO:1 or SEQ ID NO:3 by substitution, deletion, insertion and/or addition of 1 to several amino acid residues, for example 1 to 15, preferably 1 to 9, more preferably 1 to 5, more preferably 1 to 3 amino acid residues, and having a mismatch endonuclease activity; and a polypeptide having an amino acid sequence which shares at least 90% amino acid sequence identity, preferably at least 95% amino acid sequence identity with the amino acid sequence of SEQ ID NO:1 or SEQ ID NO:3, and having a mismatch endonuclease activity. For example, the homologs of the polypeptide having the amino acid sequence of SEQ ID NO:1 or SEQ ID NO:3 as mentioned above in section "(1) Heat-resistant mismatch endonuclease of the present invention and mutants thereof" are included.

The method of cleaving a double-stranded nucleic acid of the present invention may be performed in the presence of a proliferating cell nuclear antigen (PCNA) derived from a heat-resistant microorganism. Examples of PCNA that can be used in the present invention include, but not limited to, PCNA derived from the genus *Pyrococcus*, the genus *Thermococcus*, the genus *Methanopyrus*, and the genus *Methanococcus*, and their homologs. Efficiency of cleavage is enhanced by performing the cleavage of a double-stranded nucleic acid having a mismatch in the presence of PCNA.

In the cleavage method of a double-stranded nucleic acid of the present invention, a mismatched base pair is present within the double-stranded nucleic acid (between two base pairs formed by normal base-pairing). The double-stranded nucleic acid may contain one mismatched base pair, or may contain plural mismatched base pairs at intervals. Examples of the mismatched base pairs in the cleavage method of a double-stranded nucleic acid of the present invention include preferably 1 to 8 contiguous mismatched base pairs present within the double-stranded nucleic acid, more preferably 1 to 4 contiguous mismatched base pairs present within the double-stranded nucleic acid, and still more preferably 2 contiguous mismatched base pairs or one mismatched base pair present within the double-stranded nucleic acid. In the cleavage method of a double-stranded nucleic acid of the present invention, when plural mismatched base pairs are present within the double-stranded nucleic acid, the plural mismatched base pairs may be mismatched base pairs of the same kind or different kinds.

Examples of the double-stranded nucleic acid having a mismatched base pair to be targeted by the mismatch endonuclease include a nucleic acid from a biological sample, for example, a PCR product, a genomic DNA, or a fragment thereof, and a synthetic nucleic acid. The double-stranded nucleic acid having a mismatched base pair may also be a nucleic acid mixture obtained by melting and reannealing of a mixture of plural biological samples, or a mixture of a nucleic acid from a biological sample and a synthetic nucleic acid. For example, when a nucleic acid containing a mutation and a wild-type nucleic acid are mixed, melted, and reannealed, a mismatched base pair is formed and cleavage by a mismatch endonuclease occurs at the position of the mismatched base pair. After the cleavage by a mismatch endonuclease, the size of the nucleic acid fragment thus cleaved can be observed to determine the presence or absence and the position of a mutation.

(3) Amplification Method of Nucleic Acid by Use of Mismatch Endonuclease of the Present Invention Use of the mismatch endonuclease of the present invention allows mutation analysis by one-step reaction in which the mismatch endonuclease is simply added to a reaction mixture for a nucleic acid amplification method such as PCR. It is known that when the number of cycles in PCR is increased to exceed a certain number, reaction products are not increased. The main causes are depletion of dNTP added to the reaction mixture, and competition between primers and reaction products for annealing. At that time, annealing between the reaction products occurs. If a template containing a mutation and a wild-type template coexist, the reaction products amplified from these are annealed each other to generate a mismatched base pair at the mutation site. Thus, mutation analysis can be done simply by performing PCR in the presence of the mismatch endonuclease of the present invention through more cycles than usual. Specifically, the present invention provides a mutation analysis method comprising treatment of a double-stranded nucleic acid with a polypeptide having the amino acid sequence of SEQ ID NO:1 and/or SEQ ID NO:3 or a homolog thereof.

In the process of nucleic acid amplification reaction, the double-stranded nucleic acid cleavage method of the present invention can be performed. By addition of the mismatch endonuclease of the present invention to a reaction solution for nucleic acid amplification, a double-stranded nucleic acid having a mismatched base pair generated by incorporation of an incorrect nucleotide during the amplification process is cleaved. As a result, amplification of a nucleic acid having a different sequence from that of a template nucleic acid before the reaction initiation is inhibited. Thus, nucleic acid amplification with a decreased error rate is attained. Specifically, the present invention provides a nucleic acid amplification method comprising a step of cleaving a double-stranded nucleic acid having a mismatched base pair by using a polypeptide having the amino acid sequence of SEQ ID NO:1 and/or SEQ ID NO:3 or a homolog thereof. An aspect of the present invention further includes a nucleic acid amplification method comprising a step of preparing a composition comprising a composition comprising a DNA polymerase, at least one pair of oligonucleotide primers, and a polypeptide having an amino acid sequence of SEQ ID NO:1 and/or SEQ ID NO:3 or a homolog thereof, and a nucleic acid molecule as a template; and a step of reacting the composition thus obtained under suitable conditions to perform nucleic acid amplification.

Examples of the nucleic acid amplification method include, but not limited to, a method of amplifying a DNA. Examples of the method of amplifying a DNA include a polymerase chain reaction (PCR) method, a multiple displacement amplification (MDA) method, and an isothermal nucleic acid amplification method such as an ICAN method and a LAMP method.

The nucleic acid amplification method of the present invention may be combined with use of a proliferating cell nuclear antigen (PCNA) derived from a heat-resistant microorganism. Examples of PCNA that can be used in the present invention include, but not limited to, PCNA derived from the genus *Pyrococcus*, the genus *Thermococcus*, the genus *Methanopyrus*, the genus *Methanococcus*, and their homologs. Efficiency of cleavage is enhanced by performing the cleavage of a double-stranded nucleic acid having a mismatch in the presence of PCNA.

(4) Composition of the Present Invention

The composition of the present invention comprises a DNA polymerase, at least one pair of oligonucleotide primers, and a polypeptide having an amino acid sequence of SEQ ID NO:1 and/or SEQ ID NO:3, or a homolog thereof. The composition of the present invention is used in a nucleic acid amplification method. The composition of the present invention used in a nucleic acid amplification method may further contain at least one selected from the group consisting of a reaction buffer, a divalent metal ion, a deoxyribonucleotide, an oligonucleotide probe, and an intercalating dye, in addition to a DNA polymerase, at least one pair of oligonucleotide primers, and a polypeptide having an amino acid sequence of SEQ ID NO:1 and/or SEQ ID NO:3, or a homolog thereof. When the above-mentioned composition is used in nucleic acid amplification reaction, the composition may further contain a nucleic acid as a template for the nucleic acid amplification reaction. Examples of the reaction buffer used in the present invention include Good's buffers such as Tris-HCl, and HEPES-KOH, and phosphate buffers such as a sodium phosphate buffer. Preferred examples of the reaction buffer include, but not limited to, a pH 6-11 sodium phosphate buffer, and a pH 6-11 Tris-HCl buffer. Examples of the divalent metal ion include a magnesium ion, a manganese ion, a zinc ion, and a cobalt ion. The divalent metal ion may be provided as a salt form such as a chloride, a sulfate, or an acetate. For example, the composition of the present invention may contain a magnesium ion at a final concentration ranging from 0.5 to 50 mM, or a manganese ion at a final concentration ranging from 0.5 to 15 mM. As used herein, the final concentration means the concentration in a reaction solution subjected to nucleic acid amplification reaction (hereinafter, the term has the same meaning). The composition of the present invention may also contain bovine serum albumin (BSA), a surfactant, and an inorganic salt. For example, the composition of the present invention may contain BSA at a final concentration ranging from 0 to 0.2 mg/ml. Examples of the surfactant include Tween 20, Triton X-100 and NP-40. For example, the composition of the present invention may contain the surfactant at a final concentration ranging from 0 to 0.2%. Examples of the inorganic salt include sodium chloride, potassium chloride, potassium glutamate, and ammonium sulfate. For example, the composition of the present invention may contain sodium chloride at a final concentration ranging from 0 to 0.3 M, potassium chloride at a final concentration ranging from 0 to 0.2 M, potassium glutamate at a final concentration ranging from 0 to 0.6 M, or ammonium sulfate at a final concentration ranging from 0 to 0.05 M. The composition of the present invention may further contain PCNA derived from a heat-resistant microorganism. Preferred examples of PCNA include, but not limited to, PCNA derived from the genus *Pyrococcus*, the genus *Thermococcus*, the genus *Methanopyrus*, and the genus *Methanococcus*.

The concentration of a polypeptide having a mismatch endonuclease activity in the above-mentioned composition for nucleic acid amplification reaction may be determined by determining a concentration that does not inhibit a DNA amplification reaction or a concentration effective for cleavage of a mismatched based pair in each reaction system as appropriate.

As the at least one pair of primers contained in the above-mentioned composition for nucleic acid amplification reaction, two or more primers suitable for each nucleic acid amplification method are selected. These primers may be DNA primers, RNA primers, or chimeric primers, in which a part of a DNA molecule is replaced by RNA, as long as the desired amplification is attained. The primers may also be primers containing a known nucleic acid analog, and labeled primers, for example, with a fluorescent dye for the purpose of detection.

(5) Inhibition Method of Amplification of Nucleic Acid Having Specific Sequence and Detection Method of Mutation The present inventors have further found that amplification of a nucleic acid having a specific nucleotide sequence in a nucleic acid amplification reaction can be inhibited by use of the mismatch endonuclease having different substrate specificity of the present invention and a suitably designed oligodeoxyribonucleotide. Thus an aspect of the present invention also includes a method of inhibiting amplification of a nucleic acid having a specific nucleotide sequence in a nucleic acid amplification reaction, comprising a step of performing the nucleic acid amplification reaction in the presence of (a) an oligodeoxyribonucleotide which is designed to generate one to several mismatches when the oligodeoxyribonucleotide is hybridized with the nucleic acid having a specific nucleotide sequence, (b) a DNA polymerase, (c) at least one pair of primers, and (d) at least one polypeptide having a mismatch endonuclease activity. An aspect of the present invention also includes a method of preferentially amplifying a target nucleic acid, comprising inhibiting amplification of a nucleic acid having a specific nucleotide sequence different from the nucleotide sequence of the target nucleic acid in one to several nucleotides by use of the above-mentioned method of inhibiting amplification of a nucleic acid having a specific nucleotide in a nucleic acid amplification reaction.

The oligodeoxyribonucleotide in the above (a) is not particularly limited, as long as it is an oligodeoxyribonucleotide designed to generate one to several mismatches when it is hybridized with a nucleic acid having a specific nucleotide sequence. The oligodeoxyribonucleotide may be a so-called chimeric oligodeoxyribonucleotide, in which a part of a DNA molecule is replaced by RNA. The 3' end of the oligodeoxyribonucleotide may be modified so as to inhibit an extension reaction from the oligodeoxyribonucleotide by a DNA polymerase, to which the present invention is not particularly limited. Examples of the modification include amination. The oligodeoxyribonucleotide may be protected from cleavage with a deoxyribonuclease by phosphorothioation or other modifications, as long as the nucleic acid, to which the oligodeoxyribonucleotide is bound, undergoes cleavage with the polypeptide having a mismatch endonuclease activity. The oligodeoxyribonucleotide may be labeled with a fluorescent dye, a quencher or the like for the purpose of detection.

The length of the oligodeoxyribonucleotide may be appropriately determined so that the oligodeoxyribonucleotide can be hybridized with the nucleic acid having a specific nucleotide sequence under conditions of the reaction performed. The position of a mismatch generated when the oligodeoxyribonucleotide is hybridized with the nucleic acid having a specific nucleotide sequence is preferably at least 3 nucleotides away from both the 5' end and 3' end of the oligodeoxyribonucleotide.

For the method of inhibiting amplification of a nucleic acid having a specific nucleotide sequence in a nucleic acid amplification reaction of the present invention, the mismatch endonuclease having the activity of specifically cleaving a mismatch site of the present invention can be used. For example, when a heat-resistant DNA polymerase is used in a nucleic acid amplification method including a reaction at a high temperature such as a PCR method, a heat-resistant mismatch endonuclease is preferably used. In such a case, preferably used is the heat-resistant mismatch endonuclease which recognizes and cleaves a G-G, G-T, or T-T mismatch, that is, (i) a polypeptide having an amino acid sequence of SEQ ID NO:1; (ii) a polypeptide having an amino acid sequence which differs from the amino acid sequence of SEQ ID NO:1 by substitution, deletion, insertion and/or addition of 1 to several amino acid residues, for example 1 to 15, preferably 1 to 9, more preferably 1 to 5, more preferably 1 to 3 amino acid residues, and having an endonuclease activity which recognizes and cleaves a G-G, G-T, or T-T mismatch; or (iii) a polypeptide having an amino acid sequence which shares at least 95% amino acid sequence identity with the amino acid sequence of SEQ ID NO:1, and having an endonuclease activity which recognizes and cleaves a G-G, G-T, or T-T mismatch; and/or the endonuclease which recognizes and cleaves an A-A, A-C, or C-C mismatch, that is, (iv) a polypeptide having an amino acid sequence of SEQ ID NO:3; (v) a polypeptide having an amino acid sequence which differs from the amino acid sequence of SEQ ID NO:3 by substitution, deletion, insertion and/or addition of 1 to several amino acid residues, for example 1 to 15, preferably 1 to 9, more preferably 1 to 5, more preferably 1 to 3 amino acid residues, and having an endonuclease activity which recognizes and cleaves an A-A, A-C, or C-C mismatch; or (vi) a polypeptide having an amino acid sequence which shares at least 90%, preferably at least 95% amino acid sequence identity with the amino acid sequence of SEQ ID NO:3, and having an endonuclease activity which recognizes and cleaves an A-A, A-C, or C-C mismatch.

For the method of inhibiting amplification of nucleic acid having a specific nucleotide sequence in a nucleic acid amplification reaction of the present invention, a mismatch endonuclease having the activity of specifically cleaving only a double-stranded nucleic acid containing a specific mismatched base pair is more preferably used. In such a case, the nucleotide sequence whose amplification is inhibited can be limited to one kind of nucleotide sequence. For example, a polypeptide having the amino acid sequence of SEQ ID NO:1 or SEQ ID NO:3, or a homolog thereof recognizes and cleaves a double-stranded nucleic acid containing a G-G, G-T or T-T mismatch, or an A-A, A-C or C-C mismatch. Thus, when the polypeptide having the amino acid sequence of SEQ ID NO:1 or SEQ ID NO:3, or a homolog thereof is used, a double-stranded nucleic acid containing a mismatch other than the above-mentioned specific mismatches is not cleaved and does not undergo inhibition of amplification. Therefore, the polypeptide having the amino acid sequence of SEQ ID NO:1 or SEQ ID NO:3, or a homolog thereof is preferably used for the method of inhibiting amplification of a nucleic acid having a specific nucleotide sequence. Such mismatch endonucleases may be used alone or in combination depending on the nucleotide sequence whose amplification is desired to be inhibited.

In the method of inhibiting amplification of a nucleic acid having a specific nucleotide sequence in a nucleic acid amplification reaction of the present invention, the concentration of the polypeptide having a mismatch endonuclease activity may be determined by examining a concentration that does not inhibit DNA amplification reaction or a concentration effective for cleavage of a mismatched based pair in each reaction system as appropriate. The concentration of the oligodeoxyribonucleotide in (a) may be determined by optimizing the usage concentration while considering the amount of a template or amplification efficiency of the target DNA. For example, the concentration of the oligodeoxyribonucleotide can be 0.1 to 10 times the concentration of a primer used for amplification reaction.

The method of inhibiting amplification of a nucleic acid having a specific nucleotide sequence in a nucleic acid amplification reaction of the present invention can be performed in any nucleic acid amplification methods. A preferred example of the nucleic acid amplification method is, but not limited to, a method of amplifying a DNA. The present invention can be performed, for example, in a PCR method, an MDA method, or an isothermal nucleic acid amplification method such as a LAMP method or an ICAN method.

The method of inhibiting amplification of a nucleic acid having a specific nucleotide sequence in a nucleic acid amplification reaction of the present invention can be applied to amplification of any nucleic acids. When a DNA is used as a target to be amplified, examples of the DNA include a DNA present in an artificially prepared DNA mixture, a sample from environment or an organism, or a DNA mixture prepared from the above-mentioned sample. Examples of the sample from an organism include, but not limited to, samples from mammals such as human. Examples of the DNA mixture include, but not limited to, a mixture of genomic DNA fragments, a mixture of cDNAs generated from mRNAs by reverse transcription reaction, and a mixture of plural PCR products. Examples of the DNA having a specific nucleotide sequence, which is subjected to inhibition of amplification, include a reverse transcription product from an rRNA, which is not separated and remains, and a small molecular DNA, which is generated by pairing between primers. When a gene library followed by functional screening is amplified, a library capable of more efficiently searching an unknown gene can be made by inhibiting amplification of a DNA having a sequence of a known gene exhibiting a positive signal.

The method of preferentially amplifying a target nucleic acid of the present invention may further comprise a step of detecting the amplified target nucleic acid. This aspect of the present invention, as used herein, is sometimes referred to as "the detection method of the present invention". For example, according to the detection method of the present invention in which a DNA is used as a target to be detected, even when a DNA that is not a target to be detected (a DNA having a specific nucleotide sequence) exists in an excessively large amount relative to a DNA that is a target to be detected (a target DNA), amplification of the non-target DNA as a template is inhibited by virtue of the oligodeoxyribonucleotide in (a) and the polypeptide having a mismatch endonuclease activity in (d) of the method of inhibiting amplification of a nucleic acid having a specific nucleotide sequence in a nucleic acid amplification reaction of the present invention, and therefore the target DNA to be detected can be detected.

Further, the detection method of the present invention enables to distinctively detect the wild-type and the mutant-type, for example, of a nucleic acid corresponding to a gene wherein a mutation in the gene is known to be present. When the detection method of the present invention is performed using a DNA containing a wild-type nucleotide sequence as the nucleic acid having a specific nucleotide sequence, a small number of a mutant allele can be detected in the presence of an excessively large amount of the normal allele (i.e., a DNA having the wild-type nucleotide sequence). For example, the method of the present invention is useful for detection of a circulating tumor DNA, or detection of a small amount of a fetal DNA sequence contained in the mother's blood. Thus an aspect of the present invention also includes a mutation detection method comprising use of the mismatch endonuclease of the present invention. Examples of the mutation include microdeletion and point mutation. Polymorphisms generated by point mutation are called single nucleotide polymorphisms (SNPs). As used herein, a DNA having a mutant nucleotide sequence among SNPs is sometimes referred to as a DNA having a single nucleotide polymorphism mutation.

Preferred examples of the nucleic acid that can be subjected to the detection method of the present invention include, but not limited to, nucleic acids containing at least one single nucleotide polymorphism selected from the group consisting of a single nucleotide polymorphism mutation used as a tumor marker, a single nucleotide polymorphism mutation correlating with a therapeutic effect of an agent for the treatment of cancer, and a single nucleotide polymorphism mutation known to correlate with canceration of cells. Examples of SNPs include those frequently found in tumor cells, and those known to correlate with a therapeutic effect of an agent for the treatment of cancer or carcinogenesis. Examples of such SNPs include SNPs of K-ras genes, B-raf genes, and epidermal growth factor receptor (EGFR) genes. Somatic mutations in the K-ras gene are frequently found in colorectal cancer, lung adenocarcinoma, thyroid cancer, and the like. Somatic mutations in the B-raf gene are frequently found in colorectal cancer, malignant melanoma, papillary thyroid cancer, non-small cell lung cancer, lung adenocarcinoma, and the like. Somatic mutations in the EGFR gene are frequently found in various solid tumors. It is known that the treatment of a cancer with an EGFR inhibitor such as gefitinib or erlotinib is likely to be effective when the EGFR gene in the cancer tissue has a specific single nucleotide polymorphism mutation. In contrast, it is known that a cancer is likely to be resistant to an EGFR inhibitor when the K-ras gene in the cancer tissue has a single nucleotide polymorphism mutation.

The mismatch endonuclease of the present invention may be used for a mutation detection method. The detection method of the present invention may be performed using, as the material, a DNA obtained after treatment of a composition containing a methylated DNA extracted from a sample from an organism with bisulfite. According to the detection method of the present invention, detection of a small number of a methylated allele in the presence of an excessively large amount of a non-methylated allele, or detection of a small number of a non-methylated allele in the presence of an excessively large amount of a methylated allele can be performed.

As the treatment with bisulfite, a known bisulfite method, which is used for detection of a methylated DNA can be used. By the treatment, non-methylated cytosine is changed into uracil, whereas methylated cytosine is not changed. When a reaction solution treated with bisulfite is subjected to amplification by PCR, uracil is changed into thymine and methylated cytosine is changed into cytosine. In other words, detection of a small number of a methylated allele in the presence of an excessively large amount of a non-methylated allele at a specific site, and detection of a small number of a non-methylated allele in the presence of an excessively large amount of a methylated allele respectively correspond to examination of the presence of cytosine in the presence of an excessively large amount of thymine, and examination of the presence of thymine in the presence of an excessively large amount of cytosine. When amplification of an excessively large amount of DNA containing thymine or cytosine is inhibited, the presence of a small number of a methylated allele or non-methylated allele is easily examined.

For the step of detecting the target nucleic acid in the detection method of the present invention, electrophoresis, nucleotide sequence analysis, or real-time PCR using a probe such as a cycling probe or a TaqMan probe can be used. For these detection methods, conventional techniques can be directly used. In particular, use of a high resolution melting (HRM) analysis method allows amplification and detection of a DNA of interest by one step, and thus rapid and simple examination of the DNA of interest is attained.

The inhibition method of amplification of a nucleic acid having a specific sequence and the mutation detection method of the present invention may be combined with use of PCNA derived from a heat-resistant microorganism. Examples of PCNA that can be used in the present invention include, but not limited to, PCNA derived from the genus *Pyrococcus*, the genus *Thermococcus*, the genus *Methanopyrus*, and the genus *Methanococcus*, and their homologs.

An aspect of the present invention further includes a composition for a nucleic acid amplification reaction, comprising (a) an oligodeoxyribonucleotide which is designed to generate one to several mismatches when the oligodeoxyribonucleotide is hybridized with a nucleic acid having a specific nucleotide sequence, (b) a DNA polymerase, (c) at least one pair of primers, and (d) at least one polypeptide having a mismatch endonuclease activity. The composition may further contain at least one selected from the group consisting of a reaction buffer, a divalent metal ion, a deoxyribonucleotide, an oligonucleotide probe, and an intercalating dye. When the composition is used for a nucleic acid amplification reaction, the composition may further contain a nucleic acid as a template for the nucleic acid amplification reaction. The composition may also contain bovine serum albumin (BSA), a surfactant, and an inorganic salt. The composition may further contain PCNA derived from a heat-resistant microorganism.

EXAMPLES

The present invention will be more specifically explained by way of Examples, which the present invention is not limited to.

Preparation Example 1

Preparation of Genomic DNA

*Thermococcus* kodakarensis KOD1 (JCM 12380$^T$, hereinafter, referred to as TKO) was distributed from Professor Haruyuki Atomi (Kyoto University Graduate School of Engineering). KOD1 was cultured according to the following method. Sodium sulfide was added into 1 L of an artificial seawater (hereinafter, referred to as ASW)-YT medium [0.8×ASW, 5 g/L Bacto yeast extract (manufactured by DIFCO), 5 g/L Bacto trypton (manufactured by Becton, Dickinson and Company), 0.1% resazurin (manufactured by Nacalai tesque)] containing 5 g of sodium pyruvate (manufactured by Nacalai tesque) until the medium became colorless. Then, KOD1 was inoculated into the medium, anaerobically cultured at 85° C. for 16 hours, and collected. The collected KOD1 was used for subsequent experiments. Herein, the "0.8×ASW" contained in the ASW-YT medium comprises 16 g/L NaCl, 2.4 g/L MgCl$_2$.6H$_2$O, 4.8 g/L MgSO$_4$.7H$_2$O, 0.8 g/L (NH$_4$)$_2$SO$_4$, 0.16 g/L NaHCO$_3$, 0.24 g/L CaCl$_2$.2H$_2$O, 0.4 g/L KCl, 0.336 g/L KH$_2$PO$_4$, 0.04 g/L NaBr, 0.016 g/L SrCl$_2$.6H$_2$O, and 0.008 g/L Fe(NH$_4$) citrate. About 2 g of the microorganism cultured as described above was suspended in 100 ml of buffer L [10 mM Tris-HCl (pH 8.0), 1 mM EDTA, 100 mM NaCl], and 1 ml of 10% SDS was added to the suspension. The microorganism suspension thus obtained was stirred, and then 1 ml of 20 mg/mL proteinase K (manufactured by TAKARA BIO INC.) was added to the suspension. The suspension was left to stand at 55° C. for 60 minutes. The microorganism suspension treated with proteinase K was sequentially subjected to phenol extraction, phenol/chloroform extraction, and chloroform extraction. To an aqueous layer thus obtained, ethanol was added to precipitate a DNA.

The DNA was collected, and dissolved in 100 ml of a TE solution [10 mM Tris-HCl (pH 8.0), 1 mM EDTA]. To the solution thus obtained, 0.75 mg of RNase A (manufactured by Nacalai tesque) was added, and reacted at 37° C. for 60 minutes. Then, the reaction solution was sequentially subjected to phenol extraction, phenol/chloroform extraction, and chloroform extraction to obtain an aqueous layer. Then, a DAN was collected from the aqueous layer by ethanol precipitation. Finally 7.5 mg of the DNA was obtained.

Example 1: Preparation of TKO NucS (1) Preparation of Plasmid for Expression of TKO NucS A gene encoding a polypeptide having the amino acid sequence of SEQ ID NO:1, i.e., a TKO nucS gene was cloned by the following method. First, PCR was performed using 100 ng of the TKO genomic DNA prepared by Preparation Example 1 as a template, and TK1898-F having a nucleotide sequence of SEQ ID NO:5 and TK1898-R having a nucleotide sequence of SEQ ID NO:6 as primers. TK1898-F had a sequence recognized by restriction enzyme NdeI and TK1898-R had a sequence recognized by restriction enzyme NotI. A reaction solution contained 0.5 µM each primer, 2.5 mM dNTP, 1.5 mM MgCl$_2$, 1 U KOD-Plus-Neo DNA polymerase (manufactured by TOYOBO CO., LTD.), and had a reaction volume of 50 µL. PCR was performed by the reaction of 30 cycles in which one cycle consisted of 10 seconds at 98° C., 30 seconds at 55° C. and 1 minute at 68° C.

The reaction solution was electrophoresed on agarose, and a band of about 800 bp corresponding to the TKO nucS gene was excised. A DNA was purified from the band by a conventional method. The DNA was digested with restriction enzymes NdeI and NotI (manufactured by TAKARA BIO INC.), and subjected to agarose electrophoresis again. A DNA fragment was purified from the gel. The DNA fragment was mixed with pET21a (manufactured by Novagen), which was previously digested with NdeI and NotI. The mixture was subjected to a ligation reaction, and then transduced into Escherichia coli (hereinafter abbreviated as E. coli) JM109 to obtain a transformant. The transformant was cultured on an LB agar medium containing ampicillin. Then, colonies formed. The colony was cultured in an LB medium containing ampicillin to obtain bacterial cells. A plasmid was purified from the bacterial cells by using PureLink® HiPure Plasmid Midiprep kit (manufactured by Life Technologies). The nucleotide sequence of a fragment inserted in the plasmid was determined by a conventional method to confirm that the TKO nucS gene was correctly cloned. The TKO nucS gene-containing plasmid is designated pET21a-TkoNucS.

(2) Expression of TKO NucS

The pET21a-TkoNucS prepared by Example 1 (1), which was an expression plasmid for TKO NucS, was used. For production of a recombinant protein, an E. coli recombinant protein-expression system available from Novagen (pET system) was used. First, E. coli BL21-CodonPlus (DE3)-RIL (manufactured by Agilent Technologies) was transformed with pET21a-TkoNucS by a method as described in attached instructions. Transformed bacterial cells were cultured into 100 ml of an LB medium containing 50 µg/mL ampicillin and 34 µg/mL chloramphenicol until confluence. A culture solution thus obtained was inoculated into 1 L of an LB medium containing 50 µg/mL ampicillin and 34 µg/mL chloramphenicol so that OD$_{600}$ became 0.01, and cultured with shaking at 37° C. until OD$_{600}$ became 0.4. Then, production of a protein of interest was induced by addition of IPTG (final concentration: 1 mM) to the culture solution. After the addition of IPTG, the culture solution was cultured with shaking at 25° C. for 16 hours, and centrifuged (at 5,000×g, for 10 minute, at 4° C.) to collect the bacterial cells.

The collected bacterial cells were suspended in 25 ml of solution A [50 mM Tris-HCl (pH 8.0), 0.5 mM DTT, 0.1 mM EDTA, 10% glycerol] containing 0.5 M sodium chloride and 1 mM PMSF, sonicated on ice (for 10 minutes in total, by repeats of "on" for 10 seconds/"off" for 10 seconds), and then centrifuged (at 24,000×g, for 10 minute, at 4° C.) to obtain a supernatant. The supernatant was heat-treated (at 80° C., for 30 minutes) and then centrifuged (at 24,000×g, for 10 minute, at 4° C.) to remove heat-denatured proteins derived from E. coli.

(3) Purification of TKO NucS

For purification of the TKO NucS protein contained in the supernatant obtained after the heat-treatment and the centrifugation as described in above (2), polyethylenimine was added to the supernatant at a final concentration of 0.15% to insolubilize nucleic acids contaminating the supernatant. The nucleic acids were removed by centrifugation (at 24,000×g, for 10 minutes, at 4° C.) to obtain a supernatant. To the supernatant, (NH$_4$)$_2$SO$_4$ was added until 80% saturation, and the mixture was stirred at 4° C. overnight to salt out the protein of interest. A solution thus obtained was (at 24,000×g, for 10 minute, at 4° C.) to obtain a precipitate. The precipitate was dissolved in 20 ml of the solution A containing 1.5 M (NH$_4$)$_2$SO$_4$, and loaded onto hydrophobic interaction chromatography column HiTrap Phenyl HP 5 ml (manufactured by GE Healthcare) using AKTA purifier system (manufactured by GE Healthcare). Proteins were eluted by a concentration gradient of 1.5 to 0 M (NH$_4$)$_2$SO$_4$, and elution fractions corresponding to 1.4 to 0.73 M (NH$_4$)$_2$SO$_4$ were collected. These fractions were dialyzed against the solution A containing 0.3 M sodium chloride overnight. A solution obtained after the dialysis was centrifuged (at 23,708×g, for 10 minutes, at 4° C.) to obtain a supernatant. The supernatant was loaded onto affinity chromatography column HisTrap Heparin HP 1 ml (manufactured by GE Healthcare). Proteins were eluted by a concentration gradient of 0.3 M to 1 M sodium chloride, and elution fractions corresponding to 0.58 to 0.8 M sodium chloride were collected. These fractions were dialyzed against the solution A containing 0.35 M sodium chloride overnight. A solution obtained after the dialysis was centrifuged (at 24,000×g, for 10 minutes, at 4° C.) to obtain a supernatant. The supernatant was loaded onto cation exchange chromatography column HiTrap SP HP 1 ml (manufactured by GE Healthcare). Proteins were eluted by a concentration gradient of 0.35 M to 1 M sodium chloride, and elution fractions were collected as a finally purified product. The finally purified product was subjected to 12% SDS-PAGE to confirm purity. A result is shown in FIG. 1. The concentration of the purified protein was calculated from an absorbance at 280 nm, using molar absorbance coefficient ε280=12950 M$^{-1}$cm$^{-1}$ obtained by ProtParam tool (http://web.expasy.org/protparam/).

Example 2: Enzymatic Property of TKO NucS (1) Preparation of Substrates for Mismatched DNA-Cleavage Reaction Experiments for the mismatch cleavage activity of TKO NucS were performed. The nucleotide sequences of oligonucleotides used in this Example are shown in SEQ ID NOs:7-16. SEQ ID NOs:7-9 show oligonucleotides fluorescently labeled with Cy5 at their 5' ends.

As shown in FIG. 2, the oligonucleotides shown by SEQ ID NOs:7-16 were combined to prepare a 45 bp double-stranded DNA containing no mismatch (all match dsDNA), and kinds of double-stranded DNA substrates containing one mismatch site [a double-stranded DNA containing a mismatch between adenine and adenine (A-A dsDNA), a double-stranded DNA containing a mismatch between adenine and cytosine (A-C dsDNA), a double-stranded DNA containing a mismatch between adenine and guanine (A-G dsDNA), a double-stranded DNA containing a mismatch between guanine and thymine (G-T dsDNA), a double-stranded DNA containing a mismatch between guanine and guanine (G-G dsDNA), a double-stranded DNA containing a mismatch between thymine and cytosine (T-C dsDNA), a double-stranded DNA containing a mismatch between thymine and thymine (T-T dsDNA), and a double-stranded DNA containing a mismatch between cytosine and cytosine (C-C dsDNA)]. In 50 µl of anneal solution A [20 mM Tris-HCl (pH 8.0), 6 mM $(NH_4)SO_4$, 2 mM $MgCl_2$] containing an oligonucleotide fluorescently labeled with Cy5 and an unlabeled oligonucleotide at the ratio of 1 to 1.6, the mismatched oligonucleotides were annealed to prepare a 50 nM substrate solution containing a fluorescently-labeled DNA. The annealing was performed under the conditions of 5 minutes at 98° C., 30 seconds at 80° C., 30 minutes from 80° C. to 60° C., 30 seconds at 60° C., 30 minutes from 60° C. to 40° C., and 30 seconds at 25° C. Further, a combination of the labeled and unlabeled oligonucleotides as mentioned above was annealed in 50 µl of anneal solution B [20 mM Tris-HCl (pH 8.0), 100 mM NaCl, 6 mM $(NH_4)SO_4$] under the above-mentioned annealing conditions to prepare a 50 nM fluorescently-labeled DNA substrate solution that did not contain a divalent metal ion.

(2) Measurement of Mismatched DNA-Cleavage Activity

In 20 µl of a reaction solution [20 mM Tris-HCl (pH 8.0), 100 mM NaCl, 6 mM $(NH_4)SO_4$, 2 mM $MgCl_2$, 0.1% Triton X-100, 0.1 mg/mL BSA], TKO NucS at each concentration (0, 1, 2, 5, 10, 20, 50 and 100 nM as a monomer), and a substrate (G-T dsDNA) at 5 nM were reacted at 55° C. for 5 minutes. Then, 1 µl of 0.5 M EDTA was added to the reaction solution to stop the reaction. After the reaction was stopped, 0.5 µl of 5 mg/mL proteinase K was added to the reaction solution, and the reaction solution was kept for 30 minutes to degrade protein. To the reaction solution treated with proteinase K, 4 µl of a gel loading buffer [15% Ficoll, 10 mM Tris-HCl (pH 8.0), 0.1% Orange G] was added. The solution thus obtained was loaded onto a 10% polyacrylamide gel and run in 1×TBE at 25 mA for 30 minutes by electrophoresis. Results are shown in FIG. 3-A. In FIG. 3-A, lanes 1 to 8 respectively correspond to 0 to 100 nM TKO NucS. After the electrophoresis, reaction products were detected from the gel by using Typhoon Trio+ imager (manufactured by GE Healthcare), and bands corresponding to the cleaved oligonucleotides were quantitated by using Image Quant TL. Results are shown in FIG. 3-B. In FIG. 3-B, the vertical axis shows cleavage efficiency (%) and the horizontal axis shows the concentration of TKO NucS.

(3) Study of Optimum pH for Mismatched DNA-Cleavage Reaction by TKO NucS

The optimum pH for mismatched DNA-cleavage reaction by TKO NucS was examined as described below. Specifically, 2 nM TKO NucS and 5 nM G-T dsDNA shown in FIG. 2 (a double-stranded DNA consisting of a Cy5-45-mismatch oligonucleotide having the nucleotide sequence of SEQ ID NO:8 and a temp45-normal oligonucleotide having the nucleotide sequence of SEQ ID NO:10) were added to each buffer of a 20 mM Glycine-HCl buffer (pH 3.0), a 20 mM $CH_3COOH$—$CH_3COONa$ buffer (pH 4.0 and pH 5.0), a 20 mM MES-HCl buffer (pH 6.0), a 20 mM Bis-Tris-HCl buffer (pH 7.0), a 20 mM Tris-HCl buffer (pH 8.0), a 20 mM Glycine-NaOH buffer (pH 9.0 and pH 10.0), a 20 mM CAPS-NaOH buffer (pH 11.0), and a 20 mM Phosphate-NaOH buffer (pH 12.0), and a 0.1 M NaOH solution (pH 13.0), wherein the buffer and the NaOH solution contained 40 mM NaCl, 10 mM KCl, 6 mM $(NH_4)_2SO_4$, 2 mM $MgCl_2$, 0.1% Triton X-100 and 0.1 mg/mL BSA, and then incubated at 55° C. for 5 minutes. After the incubation, the reaction solution was treated with proteinase K, and then subjected to electrophoresis to determine a cleavage activity. Results are shown in FIG. 4. FIG. 4 shows optimum pH for reaction. In FIG. 4, the vertical axis shows relative activity and the horizontal axis shows pH.

(4) Effect of Kind and Concentration of Salt on Mismatched DNA-Cleavage Reaction by TKO NucS The effects of the kind and concentration of a salt on the mismatched DNA-cleavage reaction by TKO NucS were examined. First, a 20 mM Tris-HCl buffer (pH 8.0) containing 6 mM $(NH_4)_2SO_4$, 2 mM $MgCl_2$, 0.1% Triton X-100 and 0.1 mg/mL BSA was used to prepare a reaction solution containing 0, 50, 100, 150, 200, 300, 400, 600, 800, or 1000 mM NaCl, KCl or K-Glu (potassium glutamate). To the reaction solution, 2 nM TKO NucS and 5 nM G-T dsDNA were added, and then incubated at 55° C. for 5 minutes. After the incubation, the reaction solution was treated with proteinase K, and then subjected to electrophoresis to determine a cleavage activity. Results are shown in FIG. 5. FIG. 5(A) shows the effects of the concentration of sodium chloride, and the vertical axis shows relative activity and the horizontal axis shows the salt concentration. FIG. 5(B) shows the effects of the concentration of potassium chloride, and the vertical axis shows relative activity and the horizontal axis shows the salt concentration. FIG. 5(C) shows the effects of the concentration of potassium glutamate, and the vertical axis shows relative activity and the horizontal axis shows the salt concentration.

(5) Effect of Divalent Metal Ion on Mismatched DNA-Cleavage Reaction by TKO NucS The effects of divalent metal ions on the mismatched DNA-cleavage reaction by TKO NucS were examined. A 20 mM Tris-HCl buffer (pH 8.0) containing 6 mM $(NH_4)_2SO_4$, 200 mM NaCl, 0.1% Triton X-100 and 0.1 mg/mL BSA was used to prepare a reaction solution containing 0, 0.5, 2, 5, 10, 20, 50, 100 or 200 mM $MgCl_2$, or 0, 0.5, 1, 2, 5, 10 or 20 mM $MnCl_2$. To the reaction solution, 2 nM TKO NucS and 5 nM G-T dsDNA were added, and then incubated at 55° C. for 5 minutes. After the incubation, the reaction solution was treated with proteinase K, and then subjected to electrophoresis to determine a cleavage activity. Results are shown in FIG. 6 and FIG. 7. FIG. 6 shows the effects of the concentration of magnesium chloride, and the vertical axis shows relative activity, and the horizontal axis shows the concentration of 0-200 mM in (A) and the concentration of 0-20 mM in (B). FIG. 7 shows the effects of manganese chloride, and the vertical axis shows relative activity and the horizontal axis shows the manganese concentration.

(6) Study of Optimum Temperature for Mismatched DNA-Cleavage Reaction by TKO NucS The optimum temperature for mismatched DNA-cleavage reaction by TKO NucS was examined as described below. Specifically, a reaction solution containing a 20 mM Tris-HCl buffer (pH 8.0), 6 mM $(NH_4)_2SO_4$, 100 mM NaCl, 2 mM $MgCl_2$, 0.1% Triton X-100 and 0.1 mg/mL BSA was prepared. To the reaction solution, 2 nM TKO NucS and 5 nM G-T dsDNA were added, and then incubated at reaction temperature ranging from 30° C. to 95° C. for 5 minutes. After the incubation, the reaction solution was treated with proteinase K, and then subjected to electrophoresis to determine a cleavage activity. Results are shown in FIG. 8. FIG. 8 shows optimum temperature. In FIG. 8, the vertical axis shows relative activity and the horizontal axis shows reaction temperature.

Example 3: Confirmation of Mismatch Cleavage Activity of TKO NucS (1) Cleavage Activity on Various Mismatched DNAs The 45 bp double-stranded DNA containing no mismatch (all match dsDNA) and the 8 kinds of 45 bp double-stranded DNA substrates containing one mismatch site which were prepared by annealing as described in Example 2 (1) were used to examine the cleavage activity of TKO NucS on various mismatched DNAs. Specifically, in 20 µl of a reaction solution [20 mM Tris-HCl (pH 8.0), 100 mM NaCl, 6 mM $(NH_4)SO_4$, 2 mM $MgCl_2$, 0.1% Triton X-100, 0.1 mg/mL BSA], TKO NucS at each concentration (0, 1, 2, 5, 10, 20, 50 and 100 nM as a monomer), and a substrate (all match dsDNA, A-A dsDNA, A-C dsDNA, A-G dsDNA, G-T dsDNA, G-G dsDNA, T-C dsDNA, and C-C dsDNA) at 5 nM were reacted at 55° C. for 5 minutes. Then, 1 µl of 0.5 M EDTA was added to the reaction solution to stop the reaction. After the reaction was stopped, 0.5 µl of 5 mg/mL proteinase K was added to the reaction solution, and the reaction solution was kept for 30 minutes to degrade protein. To the reaction solution treated with proteinase K, 4 µl of the gel loading buffer was added. The solution thus obtained was loaded onto a 10% polyacrylamide gel and run in 1×TBE at 25 mA for 30 minutes by electrophoresis. After the electrophoresis, reaction products were detected from the gel using Typhoon Trio+ imager (manufactured by GE Healthcare), and bands corresponding to the cleaved oligonucleotides were quantitated by using Image Quant TL. Results are shown in FIG. 9. In FIG. 9, the vertical axis shows cleavage efficiency (%) and the horizontal axis shows the concentration of TKO NucS. The cleavage efficiencies of each mismatch substrate are graphed by using different marks as shown by a legend. As seen from FIG. 9, TKO NucS cleaved G-T dsDNA, G-G dsDNA, T-T dsDNA, T-C dsDNA and A-G dsDNA.

(2) Measurement of DNA-Binding Activity of TKO NucS

The DNA-binding activity of TKO NucS was examined. First, to examine substrate specificity, in 20 µl of a binding solution [20 mM Tris-HCl (pH 8.0), 100 mM NaCl, 6 mM $(NH_4)SO_4$, 2 mM $MgCl_2$, 0.1% Triton X-100, 0.1 mg/mL BSA, mM DTT], TKO NucS at each concentration (0, 1, 2, 5, 10, and 20 nM as a monomer), and a probe DNA which was prepared by using a Cy5-15 binding oligonucleotide having a nucleotide sequence of SEQ ID NO:17 and having a Cy5 fluorescent label at its 5' end, and each 15 binding oligonucleotide having a nucleotide sequence of SEQ ID NO:18-26 in combinations as shown in FIG. 10 [ssDNA (Cy5-15 binding), all match (15 bp) dsDNA, A-A (15 bp) dsDNA, A-C (15 bp) dsDNA, A-G (15 bp) dsDNA, G-T (15 bp) dsDNA, G-G (15 bp) dsDNA, T-C (15 bp) dsDNA, T-T (15 bp) dsDNA, and C-C (15 bp) dsDNA] at 5 nM were incubated at 37° C. for 5 minutes. To a reaction solution after the incubation, 4 µl of the gel loading buffer was added. The solution thus obtained was loaded onto a 8% polyacrylamide gel and run in 0.5×TBE at 25 mA for 30 minutes by electrophoresis. After the electrophoresis, a binding activity was detected by using Typhoon Trio+ imager. Results are shown in FIG. 11. In FIG. 11, lanes 1-6 and lanes 7-12 respectively correspond to 0-20 nM TKO NucS. As seen from FIG. 11, TKO NucS bound to G-T (15 bp) dsDNA, G-G (15 bp) dsDNA, and T-T (15 bp) dsDNA.

(3) Study of Heat-Resistance of TKO NucS

The heat-resistance was examined as described below. Specifically, as described in Example 3 (2), 18 µl of a reaction solution that contained TKO NucS at 2 nM as a monmer and did not contain a substrate was prepared. The reaction solution was kept at each temperature (50, 60, 70, 80, 85, 90 and 95° C.) for 30 minutes. Then, a substrate (G-T mismatch dsDNA) was added at 5 nM, and the reaction solution was reacted at 55° C. for 5 minutes. Then, 1 µl of 0.5 M EDTA was added to the reaction solution to stop the reaction. After the reaction was stopped, 0.5 µl of 5 mg/mL proteinase K was added to the reaction solution, and the reaction solution was kept for 30 minutes to degrade protein. To the reaction solution treated with proteinase K, 4 µl of the gel loading buffer was added. The solution thus obtained was loaded onto a 10% polyacrylamide gel and run in 1×TBE at 25 mA for 30 minutes by electrophoresis. After the electrophoresis, reaction products were detected from the gel by using Typhoon Trio+ imager, and bands corresponding to the cleaved oligonucleotides were quantitated by using Image Quant TL. Results are shown in FIG. 12. FIG. 12 shows heat-resistance. In FIG. 12, the vertical axis shows residual activity and the horizontal axis shows treatment temperature. As seen from FIG. 12, even after the treatment at 80° C. for 30 minutes, TKO NucS still had about 80% of mismatch cleavage activity.

Example 4: Promotion of Cleavage Activity of TKO NucS by PCNA1 Derived from *Thermococci kodakarensis*

The effect of PCNA1 derived from *T. kodakarensis* (hereinafter referred to as TKO PCNA; Genes to Cells, 2012, Vol. 1, No. 2, pp. 923-937) on the mismatched DNA cleavage reaction of TKO NucS was examined. Specifically, in 20 µl of a cleavage reaction solution C containing 400 mM sodium chloride, the wild-type TKO NucS at 2.5 nM as a dimer, a substrate DNA (G-T dsDNA) at 5 nM, and each concentration of TKO PCNA (0, 5, 10, 25, 50, 125, 250, 500, and 1250 nM as a trimer) were reacted at 55° C. for 5 minutes. Then, 1 µl of 0.5 M EDTA was added to the reaction solution to stop the reaction. After the reaction was stopped, 1 µl of 5 mg/mL proteinase K and 1 µl of 10% SDS were added to the reaction solution, and the reaction solution was kept at 50° C. for 1 hour to degrade protein.

To the reaction solution treated with proteinase K/SDS, 4.5 µl of the gel loading buffer was added. The solution thus obtained was loaded onto a 10% polyacrylamide gel and run in 1×TBE at 25 mA for 20 minutes by electrophoresis.

After the electrophoresis, reaction products were detected from the gel by using Typhoon Trio+ imager, and bands corresponding to the cleaved oligonucleotides were quantitated by using Image Quant TL. Results are shown in FIG. 13. In FIG. 13, (A) shows a photograph of native-PAGE. (B) shows the strength of the bands corresponding to the substrate and the cleaved products which are quantitated by Image Quant TL, and the vertical axis shows relative activity. The relative activity is an activity in the presence of various concentration of PCNA, relative to the activity in the absence of PCNA which is defined as 1. As seen from FIG. 13, it was found that the presence of TKO PCNA promotes the mismatch cleavage activity even in the presence of 400 mM NaCl which causes the reaction inhibition.

Example 5: Preparation of Mutant-Type TKO NucS (1) Preparation of Plasmid for Expression of Mutant-Type TKO NucS To construct a plasmid for expression of an each site-directed mutant of TKO NucS, primers having nucleotide sequences of SEQ ID NOs:27 to 30 were prepared. Then, to construct a plasmid for production of mutant-type TKO NucS, a mutagenesis using PCR was used.

To introduce mutations at position 47 and position 76, two rounds of the following procedure were performed. To two reaction solutions each (25 µl) containing 1×PCR buffer for KOD-Plus-Neo (manufactured by TOYOBO CO., LTD.), 0.2 mM each dNTP, 1.5 mM magnesium ion and 0.02 U/µL KOD-Plus-Neo, respectively, 25 ng of the plasmid for expression of TKO NucS (pET21a-TkoNucS) for the first round and 25 ng of a plasmid prepared by the first round for the second round as a template, and each 7.5 pmol of primers having nucleotide sequences of SEQ ID NOs:27 and 28 for the first round and each 7.5 pmol of primers having nucleotide sequences of SEQ ID NOs:29 and 30 for the second round were added. The reaction was performed under conditions comprising 1 minute at 98° C.; 14 cycles in which one cycle consisted of 10 seconds at 98° C., 30 seconds at 55° C. and 5 minutes at 68° C.; 5 minutes at 68° C., and then 5 seconds at 25° C.

After PCR, 0.5 µl of 20 U/µl Dpnl (manufactured by TAKARA BIO INC.) was added to the reaction solution, and reacted at 37° C. for 1 hour. The reaction solution treated with Dpni was used to transform E. coli JM109. The bacterial cells thus obtained were cultured with shaking in 25 ml of an LB medium containing 50 µg/ml of ampicillin, and then, extraction of plasmids was performed by using PureLink® HiPure Plasmid Midiprep kit. A nucleotide sequence encoding TKO NucS in the extracted plasmid was determined by a conventional method. Thus it was confirmed that a plasmid for production of the mutant-type TKO NucS protein was prepared. The plasmid thus obtained is designated pET21a-TkoNucS_S47A/N76A. The expression and purification of the mutant-type TKO NucS S47A/N76A were performed by the method described in Example 1 (2) and (3).

Example 6: Mismatched DNA-Cleavage Activity of Mutant-Type TKO NucS S47A/N76A

The mismatched DNA-cleavage activity of the mutant-type TKO NucS S47A/N76A was analyzed. Specifically, in 20 µl of a reaction solution [20 mM T s-HCl (pH 8.0), 100 mM NaCl, 6 mM (NH$_4$)SO$_4$, 2 mM MgCl$_2$, 0.1% Triton X-100, 0.1 mg/mL BSA], a substrate (A-A dsDNA) at 5 nM, and the wild-type TKO NucS or the mutant-type TKO NucS S47A/N76A at 50 nM as a dimer and were reacted at 55° C. for 5 minutes. Then, 1 µl of 0.5 M EDTA was added to the reaction solution to stop the reaction. After the reaction was stopped, 0.5 µl of 5 mg/mL proteinase K was added to the reaction solution, and the reaction solution was kept for 30 minutes to degrade protein. To the reaction solution treated with proteinase K, 4 µl of the gel loading buffer was added. The solution thus obtained was loaded onto a 10% polyacrylamide gel and run in 1×TBE at 25 mA for 30 minutes by electrophoresis.

Results are shown in FIG. 14. In FIG. 14, lanes 1 to 3 respectively correspond to the reaction solution that does not contain any TKO NucS protein, the reaction solution containing the wild-type TKO NucS, and the reaction solution containing the mutant-type TKO NucS S47A/N76A. As a result, it was found that the mutant-type TKO NucS S47A/N76A recognizes and cleaves the A-A mismatch. Thus, both a mismatch endonuclease that recognizes and cleaves a G-G, G-T or T-T mismatch, and a mismatch endonuclease that recognizes and cleaves at least an A-A mismatch were obtained.

INDUSTRIAL APPLICABILITY

The present invention is useful in broad fields including the fields of genetic technology, biology, medicine, and agriculture.

Sequence Listing Free text

SEQ ID NO: 1: amino acid sequence of wild type endonuclease NucS from *Thermococcus* kodakarensis SEQ ID NO: 2: nucleotide sequence of wild type endonuclease NucS from *Thermococcus* kodakarensis SEQ ID NO: 3: amino acid sequence of mutant endonuclease NucS from *Thermococcus* kodakarensis SEQ ID NO: 4: nucleotide sequence of mutant endonuclease NucS from *Thermococcus* kodakarensis SEQ ID NO: 5: TK1898-F primer SEQ ID NO: 6: TK1898-R primer SEQ ID NO: 7: Substrate for TKO NucS, named as Cy5-45-nondamaged. "5'-end is labeled with Cy5"

SEQ ID NO: 8: Substrate for TKO NucS, named as Cy5-45-mismatch. "5'-end is labeled with Cy5"

SEQ ID NO: 9: Substrate for TKO NucS, named as Cy5-temp45. "5'-end is labeled with Cy5"

SEQ ID NO: 10: Substrate for TKO NucS, named as temp45-normal.

SEQ ID NO: 11: Substrate for TKO NucS, named as temp45-21A.

SEQ ID NO: 12: Substrate for TKO NucS, named as temp45-21C.

SEQ ID NO: 13: Substrate for TKO NucS, named as temp45-21G.

SEQ ID NO: 14: Substrate for TKO NucS, named as 45-mismatch25C.

SEQ ID NO: 15: Substrate for TKO NucS, named as 45-mismatch25T.

SEQ ID NO: 16: Substrate for TKO NucS, named as nondamaged-22C.

SEQ ID NO: 17: Substrate for TKO NucS, named as Cy5-15binding. "5-end is labeled with Cy5"

SEQ ID NO: 18: Substrate for TKO NucS, named as 15binding_AT.

SEQ ID NO: 19: Substrate for TKO NucS, named as 15binding_AA.

SEQ ID NO: 20: Substrate for TKO NucS, named as 15binding_CA.

SEQ ID NO: 21: Substrate for TKO NucS, named as 15binding_GA.

SEQ ID NO: 22: Substrate for TKO NucS, named as 15binding_GT.

SEQ ID NO: 23: Substrate for TKO NucS, named as 15binding_GG.

SEQ ID NO: 24: Substrate for TKO NucS, named as 15binding_CT.

SEQ ID NO: 25: Substrate for TKO NucS, named as 15binding_TT.

SEQ ID NO: 26: Substrate for TKO NucS, named as 15binding_CC.

SEQ ID NO: 27: A47-F primer

SEQ ID NO: 28: A47-R primer

SEQ ID NO: 29: A76-F primer

SEQ ID NO: 30: A76-R primer

The invention claimed is:

1. A method of cleaving a double-stranded nucleic acid, comprising treating a double-stranded nucleic acid having a mismatched base pair with at least one polypeptide selected from the group consisting of the following (i) to (iii) to recognize and cleave both strands of the double-stranded nucleic acid at the position of a G-G, G-T, or T-T mismatched base pair:

(i) a polypeptide having an amino acid sequence of SEQ ID NO:1;

(ii) a polypeptide having an amino acid sequence which differs from the amino acid sequence of SEQ ID NO:1 by substitution, deletion, insertion and/or addition of 1 to several amino acid residues, and having a mismatch endonuclease activity which recognizes and cleaves a G-G, G-T, or T-T mismatch; and (iii) a polypeptide having an amino acid sequence which shares at least 95% amino acid sequence identity with the amino acid sequence of SEQ ID NO:1, and having a mismatch endonuclease activity which recognizes and cleaves a G-G, G-T, or T-T mismatch.

* * * * *